United States Patent
Weinberg et al.

(10) Patent No.: US 6,187,536 B1
(45) Date of Patent: Feb. 13, 2001

(54) METHODS OF IDENTIFYING AND DETECTING PANCREATIC CANCER

(75) Inventors: David Weinberg, Philadelphia; Scott A. Waldman, Ardmore; Michael T. Barber, Paoli; Sanjoy Biswas, Philadelphia, all of PA (US)

(73) Assignee: Thomas Jefferson University, Philadelphia, PA (US)

( * ) Notice: Under 35 U.S.C. 154(b), the term of this patent shall be extended for 0 days.

(21) Appl. No.: 09/025,534

(22) Filed: Feb. 18, 1998

Related U.S. Application Data
(60) Provisional application No. 60/038,063, filed on Feb. 18, 1997.

(51) Int. Cl.⁷ .................................................. C12Q 1/68
(52) U.S. Cl. ............................... 435/6; 435/4; 435/7.23; 436/63; 436/64
(58) Field of Search ..................... 435/4, 6, 40.5, 435/40.52, 967, 7.23; 436/63, 64

(56) References Cited

U.S. PATENT DOCUMENTS

| | | |
|---|---|---|
| 4,683,195 | 7/1987 | Mullis et al. . |
| 4,683,202 | 7/1987 | Mullis . |
| 4,963,263 | 10/1990 | Kauvar ................................. 210/635 |
| 4,965,188 | 10/1990 | Mullis et al. . |
| 4,994,258 | 2/1991 | Burns et al. . |
| 5,075,216 | 12/1991 | Innis et al. ............................... 435/6 |
| 5,128,346 | 7/1992 | Nadzan et al. ........................ 514/307 |
| 5,133,866 | 7/1992 | Kauvar ................................. 210/635 |
| 5,143,854 | 9/1992 | Pirrung et al. ........................ 436/518 |
| 5,153,191 | 10/1992 | Woodruff ............................. 514/221 |
| 5,162,336 | 11/1992 | Molino et al. ........................ 514/292 |
| 5,177,071 | 1/1993 | Freidinger et al. .................... 514/220 |
| 5,185,331 | 2/1993 | Freidinger et al. .................... 514/220 |
| 5,206,234 | 4/1993 | Bock et al. ........................... 514/213 |
| 5,206,237 | 4/1993 | Freidinger et al. .................... 514/219 |
| 5,206,238 | 4/1993 | Bock et al. ........................... 514/221 |
| 5,210,082 | 5/1993 | Bock et al. ........................... 514/213 |
| 5,217,869 | 6/1993 | Kauvar ................................. 435/7.9 |
| 5,218,114 | 6/1993 | Bock et al. ........................... 540/509 |
| 5,218,115 | 6/1993 | Bock et al. ........................... 540/509 |
| 5,220,017 | 6/1993 | Bock et al. ........................... 540/509 |
| 5,221,736 | 6/1993 | Coolidge et al. ................... 536/25.31 |
| 5,223,409 | 6/1993 | Ladner et al. ....................... 435/69.7 |
| 5,248,679 | 9/1993 | Sato et al. ............................ 514/220 |
| 5,252,743 | 10/1993 | Barrett et al. . |
| 5,264,433 | 11/1993 | Sato et al. . |
| 5,270,170 | 12/1993 | Schatz et al. . |
| 5,270,302 | 12/1993 | Shiosaki et al. . |
| 5,288,514 | 2/1994 | Ellman . |
| 5,314,886 | 5/1994 | Becker et al. . |
| 5,324,483 | 6/1994 | Cody et al. . |
| 5,338,665 | 8/1994 | Schatz et al. . |
| 5,340,474 | 8/1994 | Kauvar . |
| 5,346,907 | 9/1994 | Kerwin, Jr. et al. . |
| 5,360,802 | 11/1994 | Chambers et al. . |
| 5,366,862 | 11/1994 | Venton et al. . |
| 5,380,736 | 1/1995 | Boigegrain et al. . |
| 5,380,872 | 1/1995 | Sugg et al. . |
| 5,382,664 | 1/1995 | Sato et al. . |
| 5,384,261 | 1/1995 | Winkler et al. . |
| 5,395,750 | 3/1995 | Dillon et al. . |
| 5,405,783 | 4/1995 | Pirrung et al. . |
| 5,412,087 | 5/1995 | McGall et al. . |
| 5,420,328 | 5/1995 | Campbell . |
| 5,424,186 | 6/1995 | Fodor et al. . |
| 5,430,138 | 7/1995 | Urdea et al. . |
| 5,437,977 | 8/1995 | Segev . |
| 5,461,048 | 10/1995 | Sato et al. . |
| 5,486,597 | 1/1996 | Kalindjian et al. . |
| 5,502,164 | 3/1996 | Rosamond et al. . |
| 5,508,432 | 4/1996 | Sugg et al. . |
| 5,530,101 | 6/1996 | Queen et al. . |
| 5,534,530 | 7/1996 | Frehel et al. . |
| 5,585,089 | 12/1996 | Queen et al. . |
| 5,597,909 | 1/1997 | Urdea et al. . |

OTHER PUBLICATIONS

Zhou, W. et al. Overexpression of messenger RNA for cholecystokinin–A receptor and novel expression of messenger RNA for gastrin (cholecystokinn–B) receptor in azaserine–induced rat pancreatic carcinoma. Carcinogenesis, 14: 2189–2192, 1993.*

Mandair, K.K. et al. Cholecystokinin receptors in human pancreatic cancer cell lines. Eur. J. of Cancer, 34, 1455–1459, 1998.*

Dipiro et al. (eds.), *Pharmacotherapy: A Pathophysiologic Approach,* Elsevier Science, New York, 1989, 1384–1387.

Adams, R.D., "Anxiety, Depression, Asthenia, and Personality Disorders" in *Harrison's Principles of Internal Medicine,* McGraw–Hill Book Co., N.Y., 1983, p. 68.

Beck–Sickinger et al., "Neuropeptide Y: identification of the binding site", *Int. J. Peptide Protein Res.,* 1990, 36, 522–530.

(List continued on next page.)

*Primary Examiner*—Yvonne Eyler
*Assistant Examiner*—Anne L. Holleran
(74) *Attorney, Agent, or Firm*—Woodcock Washburn Kurtz Mackiewicz & Norris

(57) ABSTRACT

Conjugated compounds which comprises an CCK A receptor binding moiety and a radiostable active moiety are disclosed. Pharmaceutical compositions comprising conjugated compound which comprises an CCK A receptor binding moiety and a radiostable active moiety or an CCK A receptor binding moiety and a radioactive active moiety are disclosed. Methods of treating an individual suspected of suffering from pancreatic cancer are disclosed. Methods of radioimaging pancreatic cancer cells are disclosed. In vitro methods, kits and reagents are disclosed for determining whether or not an individual has pancreatic cancer cells, for determining whether tumor cells are pancreatic in origin and for analyzing tissue samples to evaluate the extent of metastasis of pancreatic tumor cells.

27 Claims, No Drawings

OTHER PUBLICATIONS

Bjorn, M.J. et al., "Evaluation of Monoclonal Antibodies for the Development of Breast Cancer Immunotoxins", *Cancer Res.*, 1985, 45, 1214–1221.

Bjorn, M.J. et al., Antibody Pseudomonas Enotoxin A Conjugates Cytotoxic to Human Breast Cancer Cells in Vittro, *Cancer Res.*, 1986, 46, 3262–3267.

Blond–Elguindi et al., "Affinity Panning of a Library of Peptides Displayed on Bacteriophages Reveals the Binding Specificity of BiP", *Cell*, 1993, 75, 717–728.

Cawley, D.B. et al., "Epidermal Growth Factor–Toxin A Chain Conjugates: EGF–Ricin A Is a Potent Toxin While EGF–Dephtheria Fragment A is Nontoxic", *Cell*, 1980, 22, 563–570.

Cull et al., "Screening for receptor ligands using large libraries of peptides linked to the C terminus of the lac repressor", *Proc. Natl. Acad. Sci. USA*, 1992, 89, 1865–1869.

Cumber, A.J. et al., "Preparation of Antibody–Toxin Conjugates", *Meth. Enz.*, 1985, 112, 207–225.

Finn, F.M. et al., "The Synthesis of Peptides by Solution Methods with Emphasis on Peptide Hormones", in *The Proteins*, vol. II, 3d Ed., Neurath, H. et al. (eds.), Academic Press, New York, NY, 1976, 105–237.

Fitzgerald, D.J.P. et al., "Adenovirus–Induced Release of Epidermal Growth Factor and Pseudomonas Toxin into the Cytosol of KB Cells during Receptor–Mediated Endocytosis", *Cell*, 1983, 32, 607–617.

Gallop et al., "Applications of Combinatorial Technologies to Drug Discovery. 1. Background and Peptide Combinatorial Libraries", *J. Med. Chem.*, 1994, 37(9), 1233–1251.

Gordon et al., "Applications of Combinatorial Technologies to Drug Discovery. 2. Combinatorial Organic Synthesis, Library Screening Strategies, and Future Directions", *J. Med.Chem.*, 1994, 37(10), 1385–1401.

Gros, O., "Biochemical Aspects of Immunotoxin Preparation", *J. Immunol. Meth.*, 1985, 81, 283–297.

Hammer et al., "Promiscuous and Allele–Specific Anchors in HLA–DR–Binding Peptides", *Cell*, 1993, 74, 197–203.

Kent et al., "Modern Methods for the Chemical Synthesis of Biologically Active Peptides", in *Synthetic Peptides in Biology and Medicine*, Alitalo, K. et al. (eds.), Elsevier Science Publishers, Amsterdam, 1985, 29–57.

Kwok et al., "Calculation of radiation doses for nonuniformly distributed β and γ radionuclides in soft tissue", *Med. Phys.*, 1985, 12(4), 405–412.

Larrick et al., "Recombinant Antibodies", *Hum. Antibod. Hybridomas*, 1991, 2, 172–189.

Magerstadt, M., *Antibody Conjugates and Malignant Disease*, CRC Press, Boca Raton, USA, 1991, 110–152.

Merrifield, "Solid Phase Peptide Synthesis. I. The Synthesis of a Tetrapeptide", *J. Am. Chem. Soc.*, 1963, 85, 2149–2154.

Ohlmeyer et al., "Complex synthetic chemical libraries indexed with molecular tags", *Proc. Natl. Acad. Sci. USA*, 1993, 90, 10922–10926.

Osteresh et al., "Libraries from libraries: Chemical transformation of combinatorial libraries to extend the range and repertoire of chemical diversity", *Proc. Natl. Acad. Sci. USA*, 1994, 91, 11138–11142.

Ruggieri et al., "Inhibition of platelet function with synthetic peptides designed to be high–affinity antagonists of fibrinogen binding to platelets", *Proc. Natl. Acad. Sci. USA*, 1986, 83, 5708–5712.

Sepetov et al., "Library of libraries: Approach to synthetic combinatorial library design and screening of "pharmacophore" motifs", *Proc. Natl. Acad. Sci. USA*, 1995, 92, 5426–5430.

Smith et al., "a ribonuclease S–peptide antagonist discovered with a bacteriophage display library", *Gene*, 1993, 128, 37–42.

Thorpe, P.E. et al., "New Coupling Agents for the Synthesis of Immunotoxins Containing a Hindered Disulfide Bone with Improved Stability in vivo", *Cancer Res.*, 1987, 47, 5924–5931.

Wang et al., "Application of Multipin Peptide Synthesis Technique for Peptide Receptor Binding Studies: Substance P as a Model System", *Bioorg. Med. Chem. Lett.*, 1993, 3(3), 447–450.

Wank, S.A. et al., "Cholecystokinin Receptor Family", *Annal. NY Acad. Sci.*, 1994, 713, 49–66.

Wessels et al., "Radionuclide selection and model absorbed dose calculations for radiolabeled tumor associated antibodies", *Med. Phys.*, 1984, 11(5), 638–645.

Wide, "Solid Phase Antigen–Antibody Systems", *Radioimmune Assay Method*, Kirkham (ed.), E. & S. Livingstone, Edinburgh, 1970, 405–413.

Winter et al., "Man–made Antibodies", *Nature*, 1991, 349, 293–299.

Worrell, N.R. et al., "Effect of linkage variation on pharmacokinetics of ricin A chain–antibody conjugates in normal rats", *Anti–Cancer Drug Design*, 1986, 1, 179–188.

Zuckerman et al., "Discovery of Nanomolar Ligands for 7–Transmembrane G–Protein–Coupled Receptors from a Diverse N–(Substituted)glycine Peptoid Library", *J. Med. Chem.*, 1994, 37, 2678–2685.

* cited by examiner

METHODS OF IDENTIFYING AND DETECTING PANCREATIC CANCER

CROSS REFERENCE TO RELATED APPLICATIONS

This application claims priority to Provisional Application Ser. No. 60/038,063 filed Feb. 18, 1997, which is incorporated herein by reference.

FIELD OF THE INVENTION

The present invention relates to compounds for and methods of identifying and imaging pancreatic cancer cells and identifying and treating individuals with pancreatic cancer.

BACKGROUND OF THE INVENTION

Pancreatic adenocarcinoma is the fifth leading cause of cancer death in the United States. The etiology of this malignancy is large unknown. Advancing age, male gender and smoking are established risk factors, while chronic pancreatitis and diabetes may be as well. The prognosis for patients with pancreatic cancer is poor, with reported 1 year survival rates between 5% and 10%.

There is considerable evidence to support a central role for cholecystokinin (CCK)* in human pancreatic cancer. The influence of endogenous hormones is well-described for several human malignancies including breast, ovary and prostate. Generally, the hormones implicated are important in both the health and disease of their target organ. CCK is an important mediator in the growth of the normal pancreas. Animal studies in which exogenous CCK was administered or endogenous CCK levels were manipulated documented pancreatic hyperplasia, dysplasia and the production of frank malignancies. Similar studies, following the induction of pancreatic tumors, suggest that CCK administration accelerates the growth of malignant compared to uninvolved tissue. In human cancer cell lines and xenografted human tumors, CCK promotes the growth of pancreatic adenocarcinoma.

Two CCK receptors have been characterized and cloned in animal and human studies, CCK-A and CCK-B. These receptors share structural homology and can be differentiated based on their binding affinities for CCK and another related gastrointestinal hormone, gastrin. The CCK-A receptor has an affinity for CCK which is 1000-fold greater than for gastrin while the CCK-B receptor exhibits equivalent affinities for either peptide.

The identification of a specific marker for pancreatic cancer would be of substantial diagnostic, and potentially therapeutic benefit. There remains a need for compositions, kits and methods for screening individuals and identifying pancreatic cancer cells. There remains a need for compositions and a method of imaging pancreatic cancer cells. There remains a need for compositions and methods for treating individuals who have pancreatic cancers.

SUMMARY OF THE INVENTION

The present invention arises out of the observation that, unlike normal human pancreas cells which express the holecystokinin receptor B (CCK B receptors)but not the holecystokinin receptor A (CCK A receptors), human ancreatic cancer cells express CCK A receptors. This finding allows for the targeting of CCK A receptors in diagnostic, imaging and therapeutic regimens related to human pancreatic cancer.

The expression of CCK A receptors in human pancreatic cancer cells may be used as a target to screen individuals for human pancreatic cancer. The CCK A receptor may serve as a human pancreatic cancer marker in samples which do not normally contain CCK A receptors from individuals, particularly those at risk of having pancreatic cancer. In patients, such as those who have been identified as having pancreatic cancer, CCK A receptors represents markers for metastatic disease.

CCK A receptors may be used as a target for imaging agents. The presence of CCK A receptors on cells can be detected in vivo using detectable ligands and the location of CCK A receptor-expressing cells can be used to determine both primary and metastic human pancreatic cancer.

The expression of CCK A receptors in human pancreatic cancer cells provides targets for delivering therapeutic compositions. The compositions may be compounds which effect the activity of CCK A receptors directly. The compositions may be or include components, portions or moieties that are ligands which selectively bind to the CCK A receptors to deliver cytotoxic or cytostatic therapeutic agents.

DESCRIPTION OF PREFERRED EMBODIMENTS OF THE INVENTION

As used herein, the term "CCK A receptor-specific ligand" and "CCK A receptor ligand" are used interchangeably and are meant to refer to compounds which bind to the human CCK A receptor at a greater affinity than they do to the human CCK B receptor.

As used herein, the term "CCK A receptor-specific antagonist" is meant to refer to compounds which bind to the human CCK A receptor at a greater affinity than they do to the human CCK B receptor and which when bound to the CCK A receptor, display less biological activity than endogenous CCK. Thus, a CCK A receptor specific antagonist competes with native CCK, and when the CCK A receptor specific antagonist is bound to CCK A receptor, either it does not transduce the signal which is transduced by CCK binding to CCK A receptor, or it transduces the signal but at a diminished level. Accordingly, the term CCK A receptor specific antagonist includes antagonists and weak agonists wherein weak a weak agonist is an agonist with less activity than endogenous CCK when bound to the CCK A receptor.

As used herein, the term "non-1,4-benzodiazepin-2-one CCK A receptor-specific antagonist" is meant to refer to CCK A receptor-specific antagonists other than those non-1,4-benzodiazepin-2-one CCK A receptor-specific antagonists disclosed in U.S. Pat. No. 4,994,258, which is incorporated herein by reference.

As used herein, the term "1,4-benzodiazepin-2-one CCK A receptor-specific antagonist" is meant to refer to CCK A receptor-specific antagonists disclosed in U.S. Pat. No. 4,994,258, which is incorporated herein by reference.

As used herein, the term "CCK A receptor-specific agonist" is meant to refer to compounds which bind to the human CCK A receptor at a greater affinity than they do to the human CCK B receptor and which when bound to the CCK A receptor, display qualitatively comparable biological activity as endogenous CCK. Thus, a CCK A receptor specific agonist competes with native CCK, and when the CCK A receptor specific antagonist is bound to CCK A receptor, either transduces the signal which is transduced by CCK binding to CCK A receptor, either to a greater, lesser or equal degree as that which is transduced by CCK. Accordingly, in some cases a CCK A receptor agonist mat be a CCK A receptor specific antagonist as defined herein provided that the agonist is a weak agonists.

As used herein, the term "active agent" is meant to refer to compounds that are therapeutic agents or imaging agents.

As used herein, the term "radiostable" is meant to refer to compounds which do not undergo radioactive decay; i.e. compounds which are not radioactive.

As used herein, the term "therapeutic agent" is meant to refer to chemotherapeutics, toxins, radiotherapeutics, targeting agents, radiosensitizing agents and antisense compounds.

As used herein, the term "chemotherapeutic" is meant to refer to compounds that, when contacted with and/or incorporated into a cell, produce an effect on the cell including causing the death of the cell, inhibiting cell division or inducing differentiation.

As used herein, the term "toxin" is meant to refer to compounds that, when contacted with and/or incorporated into a cell, produce the death of the cell.

As used herein, the term "radiotherapeutic" is meant to refer to radionuclides which when contacted with and/or incorporated into a cell, produce the death of the cell.

As used herein, the term "targeting agent" is meant to refer compounds which can be bound by and or react with other compounds. Targeting agents may be used to deliver chemotherapeutics, toxins, enzymes, radiotherapeutics, antibodies or imaging agents to cells that have targeting agents associated with them and/or to convert or otherwise transform or enhance co-administered active agents. A targeting agent may include a moiety that constitutes a first agent that is localized to the cell which when contacted. with a second agent either is converted to a third agent which has a desired activity or causes the conversion of the second agent into an agent with a desired activity. The result is the localized agent facilitates exposure of an agent with a desired activity to the cell.

As used herein, the term "radiosensitizing agent" is meant to refer to agents which increase the susceptibility of cells to the damaging effects of ionizing radiation. A radiosensitizing agent permits lower doses of radiation to be administered and still provide a therapeutically effective dose.

As used herein, the term "antisense compound" is meant to refer to a molecule which inhibits DNA transcription or RNA translation by complexing with the DNA or RNA.

As used herein, the term "imaging agent" is meant to refer to compounds which can be detected.

As used herein, the term "CCK A receptor-specific binding moiety" is meant to refer to the portion of a conjugated compound that constitutes a CCK A receptor-specific ligand.

As used herein, the term "active moiety" is meant to refer to the portion of a conjugated compound that constitutes an active agent.

As used herein, the terms "conjugated compound" and "conjugated composition" are used interchangeably and meant to refer to a compound which comprises a CCK A receptor-specific binding moiety and an active moiety and which is capable of binding to the CCK A receptor. Conjugated compounds according to the present invention comprise a portion which constitutes a CCK A receptor-specific ligand and a portion which constitutes an active agent. Thus, conjugated compounds according to the present invention are capable of specifically binding to the CCK A receptor and include a portion which is a therapeutic agent or imaging agent. Conjugated compositions may comprise crosslinkers and/or molecules that serve as spacers between the moieties.

As used herein, the terms "crosslinker", "crosslinking agent", "conjugating agent", "coupling agent", "condensation reagent" and "bifunctional crosslinker" are used interchangeably and are meant to refer to molecular groups which are used to attach the CCK A receptor-specific ligand and the active agent to thus form the conjugated compound.

As used herein, the term "pancreatic cancer" is meant to refer to human pancreatic cancer and include the well-accepted medical definition that defines pancreatic cancer as a medical condition characterized by cancer of cells of the pancreas.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. The present invention relates to methods of delivering active agents to pancreatic cancer cells including metastasized pancreatic cancer cells.

As used herein, the term "metastasized pancreatic cancer cells" is meant to refer to pancreatic cancer cells which have metastasized.

As used herein, the term "sample" is meant to refer to a sample of tissue or body fluid. In some embodiments, the sample is a sample of tissue such as lymph nodes. In some embodiments, the sample is a sample of tissue which is an adenocarcinoma of unconfirmed origin. In some embodiments, the sample is a blood sample. In some embodiments, the sample is pancreatic tissue or fluid.

As used herein, "an individual suffering from an adenocarcinoma of unconfirmed origin" is meant to refer to an individual who has a tumor in which the origin has not been definitively identified.

As used herein, "an individual is susceptible to pancreatic cancer" is meant to refer to an individual who is at a particular risk of developing pancreatic cancer. Examples of individuals at a particular risk of developing pancreatic cancer are those whose family medical history indicates above average incidence of pancreatic cancer among family members and/or those who have already developed pancreatic cancer and have been effectively treated who therefore face a risk of relapse and recurrence.

According to the present invention, the human CCK A receptor is used as a marker and target for pancreatic cancer. The CCK A receptor is found on other tissues in the human body. Thus, in diagnostic applications, the source of the sample must be from a tissue type not known to express CCK A receptors. When CCK A receptor-specific compounds are used as imaging agents, they are useful in the imaging of primary pancreatic tumors on the pancreas itself as well as to identify metastasized pancreatic cells that are metastasized to tissues and organs which do not normally express CCK A receptors.

In some preferred embodiments, the sample tested for the presence of evidence of CCK-A receptor expression is the fluid from the pancreas which can be removed by endoscopic retrograde cholangio pancreatography (ERCP) procedure. The procedure involved the removal of fluid form the ducts of the pancreas. This fluid can be analyzed to detect evidence of CCK A receptor expression, either by detecting the presence of CCK A receptors in the sample, cells that have the CCK A receptors, mRNA that encodes CCK A receptors in the sample or cells that have mRNA that encodes CCK A receptors. The presence of protein or mRNA may be accomplished by either direct or indirect methods. Patients may be screened for pancreatic cancer routinely or upon presenting symptoms by this method. This method may be used to make an initial diagnosis or to monitor treatment of patients diagnosed and treated for pancreatic cancer.

In individuals diagnosed with pancreatic cancer, it is standard therapy to suspect metastasis and aggressively attempt to eradicate metastasized cells. The present invention provides pharmaceutical compositions and methods for imaging and thereby will more definitively diagnose primary pancreatic tumors and metastasis. Further, the present invention provides pharmaceutical compositions comprising therapeutic agents and methods for specifically targeting and eliminating localized and metastasized pancreatic cancer cells. Further, the present invention provides pharmaceutical compositions that comprise therapeutics and methods for specifically eliminating pancreatic cancer cells.

According to some embodiments of the invention, therapeutics are provided for the treatment of primary and/or metastatic pancreatic cancer. The therapeutics may be used in methods of treating individuals who have pancreatic cancer alone or in conjunction with other therapies, treatments and procedures. Therapeutic compositions include CCK A receptor specific antagonists, conjugated compositions which include a CCK A receptor specific ligand conjugated to a therapeutic agent, and non-conjugated compositions in which CCK A receptor specific ligands are components in complexes which deliver therapeutic agents to the pancreatic cancer cells. In the case of conjugated compositions which include a CCK A receptor specific ligand conjugated to a therapeutic agent that is a radiotherapeutic, the CCK A receptor specific ligand is a not a 1,4-benzodiazepin-2-one CCK A receptor-specific antagonist.

CCK A receptor ligands may be identified from the compounds disclosed in U.S. Pat. No. 5,153,191, U.S. Pat. No. 5,380,736, U.S. Pat. No. 5,380,872, U.S. Pat. No. 5,502,164, U.S. Pat. Nos. 5,508,432 and 5,534,530, which are each incorporated herein by reference. dditionally CCK A receptors may be identified from the compounds disclosed in U.S. Pat. No. 5,128,346, U.S. Pat. No. 5,162,336, U.S. Pat. No. 5,177,071, U.S. Pat. No. 5,185,331, U.S. Pat. No. 5,206,234, U.S. Pat. No. 5,206,237, U.S. Pat. No. 5,206,238, U.S. Pat. No. 5,210,082, U.S. Pat. No. 5,218,114, U.S. Pat. No. 5,218,115, U.S. Pat. No. 5,220,017, U.S. Pat. No. 5,248,679, U.S. Pat. No. 5,264,433, U.S. Pat. No. 5,270,302, U.S. Pat. No. 5,314,886, U.S. Pat. No. 5,346,907, U.S. Pat. No. 5,360,802, U.S. Pat. No. 5,382,664, U.S. Pat. No. 5,461,048 and U.S. Pat. No. 5,486,597, which are each incorporated herein by reference.

CCK A receptor specific antagonists have three specific properties: 1) they have a greater affinity for CCK A receptors than they do for CCK B receptors, 2) they compete with CCK for binding to CCK A receptors, and 3) when bound to CCK A receptors, the CCK A specific antagonists do not exhibit the same biological activity as CCK does, i.e. the signal transduced by the binding of CCK to the CCK A receptor is greater than the signal transduced by the binding of a CCK A receptor specific antagonist to the CCK A receptor. Thus, weak agonists are included in the definition of CCK A receptor specific antagonists. The term weak agonist is meant to refer to an agonist with less activity than endogenous CCK when bound to the CCK A receptor. By treating an individual who has pancreatic cancer with CCK A receptor specific antagonists, the antagonists prevent CCK from transducing its signal and thereby inhibit the growth of the malignant cells.

Those having ordinary skill in the art could routinely identify compounds with the three properties set forth above. Competitive binding assays can be performed routinely to identify compounds that preferentially binds to CCK A receptors relative to CCK B receptors as well as those which compete with CCK to bind to CCK A receptors. Moreover, assays to determine the antagonist/agonist activity of such ligands compared to native CCK can be routinely performed by those having skill in the art using widely available starting materials. Accordingly, CCK A receptor specific antagonists according to the invention can be readily identified.

Examples of CCK A receptor specific antagonists include: 1) cyclic nucleotide derivatives, 2) amino acid derivatives, 3) COOH-terminal CCK peptides and modified peptides, 4) D amino acid analogs of substance P, 5) asperlicin and other benzodiazepines, 6) antibodies and antibody fragments which bind to CCK A receptors and have antagonist or weak agonist activity, and 7) other compounds of diverse structure which are reported to be effective CCK A receptor specific antagonists. In addition, those having ordinary skill in the art can routinely screen compounds and combinatorial libraries to identify CCK A receptor specific antagonists according to the invention.

CCK A receptor ligands including CCK A receptor specific agonists and CCK A receptor specific antagonists can be identified from compounds in the patents set forth above and from compounds made using combinatorial technology set forth below.

According to some embodiments of the invention, conjugated compounds are provided as therapeutics. The conjugated compositions of some embodiments of the present invention are useful for targeting cells that express CCK A receptors, particularly pancreatic cancer cells including primary and metastasized pancreatic cancer cells. Such compounds include a CCK A receptor specific ligand as a CCK A receptor specific binding moiety and a therapeutic agent as an active moiety.

The CCK A receptor specific ligand, and the conjugated compositions which include such a CCK A receptor specific ligand as a CCK A receptor specific binding moiety, binds to CCK A receptors with a greater affinity than to CCK B receptors, i.e. preferentially binds to CCK A receptors relative to CCK B receptors. In preferred embodiments, the CCK A receptor specific ligand, and the conjugated compositions which include such a CCK A receptor specific ligand as a CCK A receptor specific binding moiety, either do not bind to CCK B receptors at all or bind at very low levels relative to binding to CCK A receptors.

In addition to a CCK A receptor specific ligand as a CCK A receptor binding moiety, the conjugated composition of some embodiments of the invention also includes an active moiety which is associated with the CCK A receptor binding moiety; the active moiety being a therapeutic agent which is useful to neutralize the cell, kill the cell or render the cell more vulnerable to elimination by other agents.

According to some embodiments of the present invention, the CCK A receptor binding moiety is a CCK A receptor antagonist or a CCK A receptor agonist. The CCK A receptor binding moiety is a CCK A receptor-specific ligand and is linked to a therapeutic agent to produce a conjugated composition according to some embodiments of the present invention. Conjugated compositions are intended to be described herein as a CCK A receptor-specific ligand such as a CCK-A agonist or a CCK-A antagonist such as those described as set forth above, i.e. the cyclic nucleotide derivatives, amino acid derivatives, COOH-terminal CCK peptides and modified peptides, D amino acid analogs of substance P, asperlicin and other benzodiazepines, antibodies and antibody fragments which bind to CCK A receptors and have antagonist or weak agonist activity, and other compounds of diverse structure which are reported to be effective CCK A receptor-specific ligand as well as compounds identified as CCK A receptor-specific ligand by routine screening compounds and combinatorial libraries, linked to a therapeutic agent.

In some preferred embodiments, antibodies or fragments thereof are used as CCK A receptor specific ligands. Such antibodies are routinely produced and are preferably selected for minimal cross reactivity to the CCK B receptor. Antibodies may include monoclonal antibodies, humanized antibodies, chimeric antibodies, primatized antibodies as well as humanized Fab fragments, humanized F(Ab)2 fragments, chimeric Fab fragments, chimeric F(Ab)2 primatized fragments Fab fragments, primatized F(Ab)2 fragments. Monoclonal antibodies may be routinely produced as taught by Harlow, E. and D. Lane, (1988) *ANTIBODIES: A Laboratory Manual*, Cold Spring Harbor Laboratory, Cold Spring Harbor N.Y., which is incorporated herein by reference. Humanized antibodies may be routinely produced as taught by U.S. Pat. No. 5,585,089 and U.S. Pat. No. 5,530,101, which is incorporated herein by reference. Techniques for engineering antibodies are well known and described in Winter and Millstein (1991) *Nature* 349:293, and Larrich and Fry (1991) *Hum. Antibod. and Hybridomas* 2:17, both of which are incorporated herein by reference.

An assay may be used to test compounds to determine whether or not they are CCK A receptor specific ligands or, to test conjugated compositions to determine if they possess CCK A receptor binding activity. Such compositions that specifically bind to CCK A receptors can be identified by a competitive binding assay. The competitive binding assay is a standard technique in pharmacology which can be readily performed by those having ordinary skill in the art using readily available starting materials. Competitive binding assays, have been shown to be effective for identifying compositions that specifically bind to receptors. To identify CCK A receptor specific ligands, the assay may be modified to include the CCK B receptor to determine the relative affinity the ligand has for each receptor or a second assay is performed using the CCK B receptor and the results are compared.

Briefly, an assay to identify CCK receptor ligands consists of incubating a preparation of CCK A receptors with a constant concentration (e.g. $1 \times 10^{-10}$ M to $5 \times 10^{-10}$ M) of labeled CCK and a known concentration of a test compound. As a control, a duplicate preparation of CCK A receptors are incubated with a duplicate concentration of labeled CCK in the absence of test compound. Assays are incubated to equilibrium (2 hours) and the amount of CCK bound to receptors is quantified by standard techniques. The ability of the test compound to bind to receptors is measured as its ability to prevent (compete with) the labeled CCK from binding. Thus, in assays containing the test compound which bind to the receptor, there will be less label associated with the receptors. This assay, which is appropriate for determining the ability of any molecule to bind to CCK A receptors, is a standard competitive binding assay which can be readily employed by those having ordinary skill in the art using readily available starting materials. A parallel assay may be run using CCK B receptors instead of CCK A receptors and those ligands which preferentially bind to CCK A receptors are CCK A receptor specific ligands.

CCK A receptor specific ligands which are peptides and conjugated compositions or portions thereof which are peptides may be prepared using the solid-phase synthetic technique initially described by Merrifield, in *J. Am. Chem. Soc.*, 15:2149–2154 (1963). Other peptide synthesis techniques may be found, for example, in M. Bodanszky et al., (1976) *Peptide Synthesis*, John Wiley & Sons, 2d Ed.; Kent and Clark-Lewis in *Synthetic Peptides in Biology and Medicine*, p. 295–358, eds. Alitalo, K., et al. Science Publishers, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984), which is incorporated herein by reference. The synthesis of peptides by solution methods may also be used, as described in *The Proteins*, Vol. II, 3d Ed., p. 105–237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry*, Plenum Press, New York, N.Y. (1973), which is incorporated herein by reference. In general, these synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

CCK A receptor specific ligands that are peptides and conjugated compositions or portions thereof which are peptides may also be prepared by recombinant DNA techniques. Provision of a suitable DNA sequence encoding the desired peptide permits the production of the peptide using recombinant techniques now known in the art. The coding sequence can be obtained from natural sources or synthesized or otherwise constructed using widely available starting materials by routine methods. When the coding DNA is prepared synthetically, advantage can be taken of known codon preferences of the intended host where the DNA is to be expressed.

One having ordinary skill in the art may use well known techniques and starting materials and/or commercially available expression vectors and systems that are readily available and known in the art. See e.g., Sambrook et al.,

*Molecular Cloning a Laboratory Manual*, Second Ed. Cold Spring Harbor Press (1989).

According to the present invention, the active moiety may be a therapeutic agent or an imaging agent. One having ordinary skill in the art can readily recognize the advantages of being able to specifically target pancreatic cancer cells with a CCK A receptor ligand and conjugate such a ligand with many different active agents.

Chemotherapeutics useful as active moieties which when conjugated to a CCK A receptor binding moiety are specifically delivered to pancreatic cancer are typically, small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of chemotherapeutics include common cytotoxic or cytostatic drugs such as for example: methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platinum, vindesine (and other vinca alkaloids), mitomycin and bleomycin. Other chemotherapeutics include: purothionin (barley flour oligopeptide), macromomycin. 1,4-benzoquinone derivatives and trenimon.

Toxins are useful as active moieties. When a toxin is conjugated to a CCK A receptor binding moiety, the conjugated composition is specifically delivered to a pancreatic cancer cell by way of the CCK A receptor binding moiety and the toxin moiety kills the cell. Toxins are generally complex toxic products of various organisms including bacteria, plants, etc. Examples of toxins include but are not limited to: ricin, ricin A chain (ricin toxir.), *Pseudomonas* exotoxin (PE), diphtheria toxin (DT), *Clostrldium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin. As discussed above, when protein toxins are employed with CCK A receptor binding peptides, conjugated compositions may be produced using recombinant DNA techniques. Briefly, a recombinant DNA molecule can be constructed which encodes both the CCK A receptor specific ligand and the toxin on a chimeric gene. When the chimeric gene is expressed, a fusion protein is produced which includes a CCK A receptor specific binding moiety and an active moiety. Protein toxins are also useful to form conjugated compounds with CCK A receptor binding peptides through non-peptidyl bonds.

In addition, there are other approaches for utilizing active agents for the treatment of cancer. For example, conjugated compositions may be produced which include a CCK A binding moiety and an active moiety which is an active enzyme. The CCK A receptor specific binding moiety specifically localizes the conjugated composition to the tumor cells. An inactive prodrug which can be converted by the enzyme into an active drug is administered to the patient. The prodrug is only converted to an active drug by the enzyme which is localized to the tumor. An example of an enzyme/prodrug pair includes alkaline phosphatase/ etoposidephosphate. In such a case, the alkaline phosphatase is conjugated to a CCK A receptor specific binding ligand. The conjugated compound is administered and localizes at the pancreatic cell. Upon contact with etoposidephosphate (the prodrug), the etoposidephosphate is converted to etoposide, a chemotherapeutic drug which is taken up by the cancer cell.

Radiosensitizing agents are substances that increase the sensitivity of cells to radiation. Examples of radiosensitizing agents include nitroimidazoles, metronidazole and misonidazole (see: DeVita, V. T. Jr. in *Harrison's Principles of Internal Medicine*, p.68, McGraw-Hill Book Co., N.Y. 1983, which is incorporated herein by reference). The conjugated compound that comprises a radiosensitizing agent as the active moiety is administered and localizes at the metastasized cell. Upon exposure of the individual to radiation, the radiosensitizing agent is "excited" and causes the death of the cell.

Radionuclides may be used in pharmaceutical compositions that are useful for radiotherapy or imaging procedures. Whenever radionuclides are used as active agents, the CCK A receptor binding ligand is not a 1,4-benzodiazepin-2-one CCK A receptor-specific antagonist.

Examples of radionuclides useful as toxins in radiation therapy include: $^{47}Sc$, $^{67}CU$, $^{90}Y$, $^{109}Pd$, $^{123}I$, $^{125}I$, 131I, $^{186}Re$, $^{188}Re$, $^{199}Au$, $^{211}At$, $^{212}Pb$ and $^{212}B$. Other radionuclides which have been used by those having ordinary skill in the art include: $^{32}P$ and $^{33}P$, $^{71}Ge$, $^{77}As$, $^{103}Pb$, $^{105}Rh$, $^{111}Ag$, $^{119}Sb$, $^{121}Sn$, $^{131}Cs$, $^{143}Pr$, $^{161}Tb$, $^{177}Lu$, 191Os, $^{193M}Pt$, $^{197}Hg$, all beta negative and/or auger emitters. Some preferred radionuclides include: $^{90}Y$, $^{131}I$ $^{211}At$ and $^{212}Pb/^{212}Bi$.

According to the present invention, the active moieties may be an imaging agent. Imaging agents are useful diagnostic procedures as well as the procedures used to identify pancreatic tumors and/or the location of metastasized pancreatic cancer cells. Imaging can be performed by many procedures well-known to those having ordinary skill in the art and the appropriate imaging agent useful in such procedures may be conjugated to a CCK A receptor specific ligand by well-known means. Imaging can be performed, for example, by radioscintigraphy, nuclear magnetic resonance imaging (MRI) or computed tomography (CT scan). The most commonly employed radionuclide imaging agents include radioactive iodine and indium. Imaging by CT scan may employ a heavy metal such as iron chelates. MRI scanning may employ chelates of gadolinium or manganese. Additionally, positron emission tomography (PET) may be possible using positron emitters of oxygen, nitrogen, iron, carbon, or gallium. Example of radionuclides useful in imaging procedures include: $^{43}K$, $^{52}Fe$, $^{57}Co$, $^{67}Cu$, $^{67}Ga$, $^{68}Ga$, $^{77}Br$, $^{81}Rb/^{81M}Kr$, $^{87M}Sr$, $^{99M}Tc$, $^{111}In$, $^{113M}In$, $^{123}I$, $^{125}I$, $^{127}CS$, $^{129}Cs$, 131I, $^{132}I$, $^{197}Hg$, $^{203}Pb$ and $^{206}Bi$.

In some embodiments, it is preferred that the conjugated compositions be non-immunogenic or immunogenic at a very low level. Accordingly, it is preferred that the CCK A receptor specific binding moiety be a small, poorly immunogenic or non-immunogenic protein, peptide or a non-peptide. Likewise, it is preferred that the active moiety be a small, poorly-immunogenic or non-immunogenic protein, peptide or a non-peptide.

CCK A receptor specific ligands are conjugated to active agents by a variety of well-known techniques readily performed without undue experimentation by those having ordinary skill in the art. The technique used to conjugate the CCK A receptor specific ligand to the active agent is dependent upon the molecular nature of the CCK A receptor specific ligand and the active agent. After the CCK A receptor specific ligand and the active agent are conjugated to form a single molecule, assays may be performed to ensure that the conjugated molecule retains the activities of the moieties. The CCK A receptor specific binding assay described above may be performed using the conjugated compound to test whether it is capable of preferentially binding to the CCK A receptor. Similarly, the activity of the active moiety may be tested using various assays for each respective type of active agent. Radionuclides retain there activity, i.e. their radioactivity, irrespective of conjugation. With respect to active agents which are toxins, drugs and targeting agents, standard assays to demonstrate the activity of unconjugated forms of these compounds may be used to confirm that the activity has been retained.

Conjugation may be accomplished directly between the CCK A receptor specific ligand and the active agent or linking, intermediate molecular groups may be provided between the CCK A receptor specific ligand and the active agent. Crosslinkers are particularly useful to facilitate conjugation by providing attachment sites for each moiety. Crosslinkers may include additional molecular groups which serve as spacers to separate the moieties from each other to prevent either from interfering with the activity of the other.

One having ordinary skill in the art may conjugate a CCK A receptor specific ligand to a chemotherapeutic drug using well-known techniques. For example, Magerstadt, M. *Antibody Conjugates and Malignant Disease.* (1991) CRC Press, Boca Raton, USA, pp. 110–152) which is incorporated herein by reference, teaches the conjugation of various cytostatic drugs to amino acids of antibodies. Such reactions may be applied to conjugate chemotherapeutic drugs to CCK A recepto specific ligands with an appropriate linker. CCK A receptor specific ligands which have a free amino group may be conjugated to active agents at that group. Most of the chemotherapeutic agents currently in use in treating cancer possess functional groups that are amenable to chemical crosslinking directly with proteins. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to the single free amino group of a CCK A receptor specific ligand. For example, one procedure for crosslinking CCK A receptor specific ligands which have a free amino group to active agents which have a free amino group such as methotrexate, doxorubicin, daunorubicin, cytosinarabinoside, cis-platin, vindesine, mitomycin and bleomycin, or alkaline phosphatase, or proteinor peptide-based toxin employs homobifunctional succinimidyl esters, preferably with carbon chain spacers such as disuccinimidyl suberate (Pierce Co, Rockford, Ill.). In the event that a cleavable conjugated compound is required, the same protocol would be employed utilizing 3,3'-dithiobis (sulfosuccinimidylpropionate; Pierce Co.).

One having ordinary skill in the art may conjugate a CCK A receptor specific ligand to a radionuclide using well-known techniques. For example, Magerstadt, M. (1991) *Antibody Conjugates And Malignant Disease*, CRC Press, Boca Raton, Fla.; and Barchel, S. W. and Rhodes, B. H., (1983) *Radioimaging and Radiotherapy*, Elsevier, New York, N.Y., each of which is incorporated herein by reference, teach the conjugation of various therapeutic and diagnostic radionuclides to amino acids of antibodies. Such reactions may be applied to conjugate radionuclides to CCK A receptor specific ligand ligands with an appropriate linker.

The present invention provides pharmaceutical compositions that comprise the conjugated compounds of the invention and pharmaceutically acceptable carriers or diluents. The pharmaceutical composition of the present invention may be formulated by one having ordinary skill in the art. Suitable pharmaceutical carriers are described in *Remington's Pharmaceutical Sciences*, A. Osol, a standard reference text in this field, which is incorporated herein by reference. In carrying out methods of the present invention, conjugated compounds of the present invention can be used alone or in combination with other diagnostic, therapeutic or additional agents. Such additional agents include excipients such as coloring, stabilizing agents, osmotic agents and antibacterial agents.

The conjugated compositions of the invention can be, for example, formulated as a solution, suspension or emulsion in association with a pharmaceutically acceptable parenteral vehicle. Examples of such vehicles are water, saline, Ringer's solution, dextrose solution, and 5% human serum albumin. Liposomes may also be used. The vehicle may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions of the present invention may be administered by any means that enables the conjugated composition to reach the targeted cells. In some embodiments, routes of administration include those selected from the group consisting of intravenous, intraarterial, intraperitoneal, local administration into the blood supply of the organ in which the tumor resides or directly into the tumor itself. Intravenous administration is the preferred mode of administration. It may be accomplished with the aid of an infusion pump.

The dosage administered varies depending upon factors such as: the nature of the active moiety; the nature of the conjugated composition; pharmacodynamic characteristics; its mode and route of administration; age, health, and weight of the recipient; nature and extent of symptoms; kind of concurrent treatment; and frequency of treatment.

Because conjugated compounds are specifically targeted to cells with CCK A specific receptors, conjugated compounds which comprise chemotherapeutics or toxins are administered in doses less than those which are used when the chemotherapeutics or toxins are administered as unconjugated active agents, preferably in doses that contain up to 100 times less active agent. In some embodiments, conjugated compounds which comprise chemotherapeutics or toxins are administered in doses that contain 10–100 times less active agent as an active moiety than the dosage of chemotherapeutics or toxins administered as unconjugated active agents. To determine the appropriate dose, the amount of compound is preferably measured in moles instead of by weight. In that way, the variable weight of different CCK A receptor specific binding moieties does not affect the calculation. Presuming a one to one ratio of CCK A receptor specific binding moiety to active moiety in conjugated compositions of the invention, less moles of conjugated compounds may be administered as compared to the moles of unconjugated compounds administered, preferably up to 100 times less moles.

Typically, chemotherapeutic conjugates are administered intravenously in multiple divided doses. Up to 20 gm IV/dose of methotrexate is typically administered in an unconjugated form. When methotrexate is administered as the active moiety in a conjugated compound of the invention, there is a 10-to 100-fold dose reduction. Thus, presuming each conjugated compound includes one molecule of methotrexate conjugated to one CCK A receptor specific binding moiety, of the total amount of conjugated compound administered, up to about 0.2–2.0 g of methotrexate is present and therefore administered. In some embodiments, of the total amount of conjugated compound administered, up to about 200 mg–2 g of methotrexate is present and therefore administered.

To dose conjugated compositions comprising CCK A receptor specific binding moieties linked to active moieties that are radioisotopes in pharmaceutical compositions useful as imaging agents, it is presumed that each CCK A receptor specific binding moiety is linked to one radioactive active moiety. The amount of radioisotope to be administered is dependent upon the radioisotope. Those having ordinary skill in the art can readily formulate the amount of conjugated compound to be administered based upon the specific activity and energy of a given radionuclide used as an active moiety. Typically 0.1–100 millicuries per dose of imaging agent, preferably 1–10 millicuries, most often 2–5 millicuries are administered. Thus, pharmaceutical compositions according to the present invention useful as imaging agents which comprise conjugated compositions comprising a CCK A receptor specific binding moiety and a radioactive moiety comprise 0.1–100 millicuries, in some embodiments preferably 1–10 millicuries, in some embodiments preferably 2–5 millicuries, in some embodiments more preferably 1–5 millicuries. Examples of dosages include: $^{131}$I=between about 0.1–100 millicuries per dose, in some embodiments preferably 1–10 millicuries, in some embodiments 2–5 millicuries, and in some embodiments about 4 millicuries; $^{111}$In=between about 0.1–100 millicuries per dose, in some embodiments preferably 1–10 millicuries, in some embodiments 1–5 millicuries, and in some embodiments about 2 millicuries; $^{99m}$Tc=between about 0.1–100 millicuries per dose, in some embodiments preferably 5–75 millicuries, in some embodiments 10–50 millicuries, and in some embodiments about 27 millicuries. Depending upon the specific activity of the radioactive moiety and the weight of the CCK A receptor specific binding moiety the dosage defined by weight varies.

To dose conjugated compositions comprising CCK A receptor specific binding moieties linked to active moieties that are radioisotopes in pharmaceutical compositions useful as therapeutic agents, it is presumed that each CCK A receptor specific binding moiety is linked to one radioactive active moiety. The amount of radioisotope to be administered is dependent upon the radioisotope. Those having ordinary skill in the art can readily formulate the amount of conjugated compound to be administered based upon the specific activity and energy of a given radionuclide used as an active moiety. For therapeutics that comprise $^{131}$I, between 10–1000 nM, preferably 50–500, more preferably about 300 nanomoles of $^{131}$I at the tumor, per gram of tumor, is desirable.

Wessels B. W. and R. D. Rogus (1984) *Med. Phys.* 11:638 and Kwok, C. S. et al. (1985) Med. Phys. 12:405, both of which are incorporated herein by reference, disclose detailed dose calculations for diagnostic and therapeutic conjugates which may be used in the preparation of pharmaceutical compositions of the present invention which include radioactive conjugated compounds.

One aspect of the present invention relates to a method of treating individuals who have pancreatic cancer. Such individuals may be treated by administering to the individual a pharmaceutical composition that comprises a pharmaceutically acceptable carrier or diluent and a conjugated compound that comprises a CCK A receptor specific binding moiety and an active moiety wherein the active moiety is a radiostable therapeutic agent. In some embodiments of the present invention, the pharmaceutical composition comprises a pharmaceutically acceptable carrier or diluent and a conjugated compound that comprises a CCK A receptor specific binding moiety and an active moiety wherein the active moiety is a radiostable active agent and the CCK A receptor specific binding moiety is an antibody. In some embodiments of the present invention, the pharmaceutical composition comprises a pharmaceutically acceptable carrier or diluent and a conjugated compound that comprises a CCK A receptor specific binding moiety and an active moiety wherein the active moiety is a radiostable active agent and the CCK A receptor specific binding moiety. The CCK A receptor binding moiety may be a monoclonal antibodies, humanized antibodies, chimeric antibodies, primatized antibodies as well as humanized Fab fragments, humanized F(Ab)2 fragments, chimeric Fab fragments, chimeric F(Ab)2 Primatized fragments Fab fragments, primatized F(Ab)2 fragments. In some embodiments of the present invention, the CCK A receptor specific binding moiety is asperlicin or L-364,718/MK-329. In some embodiments of the present, the active moiety wherein the active moiety is a radiostable active agent selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, *Pseudomonas* exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole.

The pharmaceutical composition contains a therapeutically effective amount of the conjugated composition. A therapeutically effective amount is an amount which is effective to cause a cytotoxic or cytostatic effect on pancreatic cancer cells without causing lethal side effects to the individual.

One aspect of the present invention relates to a method of treating individuals who have pancreatic cancer. Such individuals may be treated by administering to the individual a pharmaceutical composition that comprises a pharmaceutically acceptable carrier or diluent and a conjugated compound that comprises a CCK A receptor specific binding moiety and an active moiety wherein the active moiety is a radioactive. According to such aspects of the invention, the CCK-A receptor binding moiety is not a 1,4-benzodiazepin-2-one CCK A receptor-specific antagonist. In some embodiments of the present invention, the pharmaceutical composition comprises a pharmaceutically acceptable carrier or diluent and a conjugated compound that comprises a CCK A receptor specific binding moiety and an active moiety wherein the active moiety is a radioactive and the CCK A receptor specific binding moiety is a CCK A receptor ligand. In some embodiments of the present invention, the pharmaceutical composition comprises a pharmaceutically acceptable carrier or diluent and a conjugated compound that comprises a CCK A receptor specific binding moiety and an active moiety wherein the active moiety is a radioactive. In some embodiments of the present invention, the pharmaceutical composition comprises a pharmaceutically acceptable carrier or diluent and a conjugated compound that comprises a CCK A receptor specific binding moiety and an active moiety wherein the active moiety is a radioactive agent selected from the group consisting of: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P, $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt $^{197}$Hg, and all beta negative and/or auger emitters.

The pharmaceutical composition contains a therapeutically effective amount of the conjugated composition. A therapeutically effective amount is an amount which is effective to cause a cytotoxic or cytostatic effect on pancreatic cancer cells without causing lethal side effects to the individual.

One aspect of the present invention relates to a method of detecting pancreatic cancer cells in an individual suspected of suffering from pancreatic cancer by radioimaging. Such individuals may be diagnosed as suffering from pancreatic cancer and pancreatic cancer cells may be detected by administering to the individual, preferably by intravenous administration, a pharmaceutical composition that comprises a pharmaceutically acceptable carrier or diluent and a conjugated compound that comprises a CCK A receptor specific binding moiety and an active moiety wherein the active moiety is a radioactive and detecting the presence of a localized accumulation or aggregation of radioactivity, indicating the presence of cells with CCK A receptors. In some embodiments of the present invention, the pharmaceutical composition comprises a pharmaceutically acceptable carrier or diluent and a conjugated compound that comprises a CCK A receptor specific binding moiety and an active moiety wherein the active moiety is a radioactive and the CCK A receptor specific binding moiety is CCK A receptor ligand. In some embodiments of the present invention, the pharmaceutical composition comprises a pharmaceutically acceptable carrier or diluent and a conjugated compound that comprises a CCK A receptor specific binding moiety and an active moiety wherein the active moiety is a radioactive agent selected from the group consisting of: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99}$MTc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi.

The pharmaceutical composition contains a diagnostically effective amount of the conjugated composition. A diagnostically effective amount is an amount: which can be detected at a site in the body where cells with CCK A receptors are located without causing lethal side effects to the individual.

Another aspect of the invention relates to unconjugated compositions which comprise a CCK A receptor binding ligand and an active agent. For example, liposomes are small vesicles composed of lipids. Drugs can be introduced into the center of these vesicles. The outer shell of these vesicles comprise a CCK A receptor specific binding ligand. Liposomes Volumes 1, 2 and 3 CRC Press Inc. Boca Raton Fla., which is incorporated herein by reference, disclose preparation of liposome-encapsulated active agents which include targeting agents that correspond to a CCK A receptor specific ligand in the outer shell. Unconjugated compositions which comprise a CCK A receptor specific ligand in the matrix of a liposome with an active agent inside include such compositions in which the active agent is selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, *Pseudomonas* exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole.

Another aspect of the invention relates to unconjugated and conjugated compositions which comprise a CCK A receptor specific receptor ligand used to deliver therapeutic nucleic acid molecules to cells that comprise a CCK A receptor such as pancreatic cancer cells. In some embodiments, the genetic material delivered to cells encodes either an antigen that can be targeted by the immune system or a protein which kills the cell or inhibits its proliferation. In some embodiments, the CCK A receptor specific ligand is used to deliver nucleic acids that encode nucleic acid molecules which replace defective endogenous genes or which encode therapeutic proteins.

In some embodiments, the CCK A receptor specific ligand is combined with or incorporated into a delivery vehicle thereby converting the delivery vehicle into a specifically targeted delivery vehicle. For example, a CCK A receptor specific binding peptide may be integrated into the outer portion of a viral particle making such a virus a CCK A receptor-bearing cell specific virus. Similarly, the coat protein of a virus may be engineered such that it is produced as a fusion protein which includes an active CCK A receptor specific binding peptide that is exposed or otherwise accessible on the outside of the viral particle making such a virus a CCK A receptor-bearing cell-specific virus. In some embodiments, a CCK A receptor specific ligand may be integrated or otherwise incorporated into the liposomes herein the CCK A receptor specific ligand is exposed or therwise accessible on the outside of the liposome making such liposomes specifically targeted to CCK A receptor-bearing cells.

The active agent in the conjugated or unconjugated compositions according to this aspect of the invention is a nucleic acid molecule. The nucleic acid may be RNA or preferably DNA. In some embodiments, the nucleic acid molecule is an antisense molecule or encodes an antisense sequence whose presence in the cell inhibits production of an undesirable protein. In some embodiments, the nucleic acid molecule encodes a ribozyme whose presence in the cell inhibits production of an undesirable protein. In some embodiments, the nucleic acid molecule encodes a protein or peptide that is desirably produced in the cell. In some embodiments, the nucleic acid molecule encodes a functional copy of a gene that is defective in the targeted cell. The nucleic acid molecule is preferably operably linked to regulatory elements needed to express the coding sequence in the cell.

Liposomes are small vesicles composed of lipids. Genetic constructs which encode proteins that are desired to be expressed in CCK A receptor-bearing cells are introduced into the center of these vesicles. The outer shell of these vesicles comprise a CCK A receptor specific ligand. Liposomes Volumes 1, 2 and 3 CRC Press Inc. Boca Raton Fla., which is incorporated herein by reference, disclose preparation of liposome-encapsulated active agents which include antibodies in the outer shell. In the present invention, anti-CCK A antibodies may be incorporated in the outer shell. Unconjugated compositions may comprise a CCK A receptor specific ligand in the matrix of a liposome with an active agent inside.

Such compositions may be used to treat may be used individuals with pancreatic cancer.

Preparation of genetic constructs is with the skill of those having ordinary skill in the art. The present invention allows such construct to be specifically targeted by using the CCK A receptor specific ligands of the present: invention. The compositions of the invention include a CCK A receptor specific ligand associated with a delivery vehicle and a gene construct.

In addition to imaging and therapeutic compositions, systems, methods and kits, the present invention relates to compositions, kits and methods useful in the in vitro screening, diagnosis and analysis of patients and patient samples. The compositions, kits and methods of the invention useful for in vitro screening, diagnosis and analysis of patient and patient samples can be used to detect indicia of CCK A receptor protein expression. The expression of CCK A receptors is indicative of possible pancreatic cancer, especially if the sample is pancreatic tissue or and/or fluid and/or when the information is used in conjunction with other information.

The present invention relates to methods, compositions and kits useful in the in vitro screening, diagnosis and analysis of patient and patient pancreatic tissue samples to detect CCK A receptor expression in pancreatic samples wherein expression of CCK A receptors in pancreatic samples such as pancreatic tissue or pancreatic fluid indicates and/or confirms pancreatic cancer.

The present invention relates to methods, compositions and kits useful in the in vitro screening, diagnosis and analysis of patient and patient samples to detect CCK A receptor expression in tumor cells wherein the presence of cells that express CCK A receptor indicates and/or confirms that a tumor of unknown origin is pancreatic cancer.

The present invention relates to methods, compositions and kits useful in the in vitro screening, diagnosis and analysis of patient and patient samples to detect the presence of CCK A receptors in a sample wherein the presence of CCK A receptor indicates and/or confirms pancreatic cancer.

In vitro screening and diagnostic compositions, methods and kits can be used in the monitoring of individuals who are in high risk groups for pancreatic cancer such as those who have been diagnosed with localized disease and/or metastasized disease and/or those who are genetically predisposed to develop the disease. In vitro screening and diagnostic compositions, methods and kits can be used in the monitoring of individuals who are undergoing and/or have been treated for localized pancreatic cancer to determine if the cancer has metastasized. In vitro screening and diagnostic compositions, methods and kits can be used in the monitoring of individuals who are undergoing and/or have been treated for pancreatic cancer to determine if the cancer has been eliminated. In vitro screening and diagnostic compositions, methods and kits can be used in the monitoring of individuals who are otherwise susceptible, i.e. individuals who have been identified as genetically predisposed such as by genetic screening and/or family histories. Advancements in the understanding of genetics and developments in technology as well as epidemiology allow for the determination of probability and risk assessment an individual has for developing pancreatic cancer. Using family health histories and/or genetic screening, it is possible to estimate the probability that a particular individual has for developing certain types of cancer including pancreatic cancer. Those individuals that have been identified as being predisposed to developing a particular form of cancer can be monitored or screened to detect evidence of pancreatic cancer. Upon discovery of such evidence, early treatment can be undertaken to combat the disease. Accordingly, individuals who are at risk for developing pancreatic cancer may be identified and samples may be isolated from such individuals. The invention is particularly useful for monitoring individuals who have been identified as having family medical histories which include relatives who have suffered from pancreatic cancer. Likewise, the invention is particularly useful to monitor individuals who have been diagnosed as having pancreatic cancer and, particularly those who have been treated and had tumors removed and/or are otherwise experiencing remission including those who have been treated for pancreatic cancer.

In vitro screening and diagnostic compositions, methods and kits can be used in the analysis of tumors. Expression of CCK A receptor is a marker for pancreatic cancer and allows for the identification of the origin of adenocarcinoma of unconfirmed origin as pancreatic tumors as well as allowing for an initial diagnosis of pancreatic cancer to be made or confirmed. Tumors believed to be pancreatic in origin can be confirmed as such using the compositions, methods and kits of the invention. The invention can be used to confirm the diagnosis of pancreatic cancer by confirming that tumors are of pancreatic origin. Similarly, tumors of unknown origin can be analyzed and identified as being pancreatic in origin using the compositions, methods and kits of the invention. The invention can be used to identify pancreatic tumors in samples of tumors removed from individuals suffering from adenocarcinomas of unconfirmed origin.

In vitro screening and diagnostic compositions, kits and methods of the invention can be used to analyze tissue samples from the pancreas to identify the presence of CCK A receptors or mRNA that encodes CCK A receptor protein directly in samples or in cells in samples.

In some embodiments of the invention, tissue and fluid samples or tumor samples may be screened to identify the presence or absence of the CCK A receptor protein. Techniques such as CCK A receptor/CCK A receptor specific ligand binding assays, ELISA assays and Western blots may be performed to determine whether the CCK A receptor is present in a sample.

In some embodiments of the invention, tissue and fluid samples or tumor samples may be screened to identify whether CCK A receptor protein is being expressed in cells in said sample by detecting the presence or absence of mRNA tLat encodes the CCK A receptor protein. The presence of mRNA that encodes the CCK A receptor protein or cDNA generated therefrom can be determined using techniques such as PCR amplification, branched chain oligonucleotide hybridization, Northern Blots (mRNA), Southern Blots (cDNA), or oligonucleotide hybridization.

In some embodiments of the invention, cells of tissue samples, including pancreatic tissue samples, or tumor samples may be examined to identify the presence or absence of the CCK A receptor protein. Techniques such as CCK A receptor/CCK A receptor specific ligand binding assays or immunohistochemistry blots may be performed on tissue sections to determine whether the CCK A receptor is present in a sample.

In some embodiments of the invention, cells of tissue samples, including pancreatic tissue samples, or tumor samples may be examined to determine whether CCK A receptor protein is being expressed in cells in the sample by detecting the presence or absence of mRNA that encodes the CCK A receptor protein. The presence of mRNA that encodes the CCK A receptor protein or cDNA generated therefrom in cells from tissue sections can be determined using techniques such as in situ hybridization.

The presence of CCK A receptors in tissue and fluid samples that do not normally express CCK A receptor indicates the possibility of pancreatic cancer. The presence of CCK A receptor in a tumor sample or on tumor cells indicates that the tumor may be pancreatic in origin. The presence of mRNA that encodes CCK A receptor in tissue and fluid samples that do not normally express CCK A receptor indicates the possibility of pancreatic cancer. The presence of mRNA that encodes CCK A receptor in tumor samples and tumor cells indicates that the tumor may be pancreatic in origin.

Samples from tumors may be identified as pancreatic in origin by identification of expression of CCK A receptors using the methods of the invention. Samples of tumors removed from individuals suffering from adenocarcinomas of unconfirmed origin can be tested to determine whether or not they possess CCK A receptor protein or mRNA encoding CCK A receptor protein.

Samples may be obtained from resected tissue or biopsy material including needle biopsy. Tissue section preparation for surgical pathology may be frozen and prepared using standard techniques. Binding assays including immunohistochemistry and in situ hybridization binding assays on tissue sections are performed in fixed cells. Alternatively, samples may be homogenized by standard techniques such as sonication, mechanical disruption or chemical lysis such as detergent lysis. It is also contemplated that tumor samples in body fluids such as blood, urine, lymph fluid, cerebral spinal fluid, amniotic fluid, vaginal fluid, semen and stool samples as well as pancreatic fluid may also be screened to determine if such tumors is pancreatic in origin. In some preferred embodiment, the sample is a fluid sample removed from the pancreas be ERCP.

Tissue samples may be obtained from any tissue except those that normally express CCK A receptors. Thus if the CCK A receptor protein or mRNA encoding the CCK A receptor protein are detected in such samples, the possibility of the presence of pancreatic cancer cells is indicated. In some preferred embodiments, the tissue samples are lymph nodes or pancreatic tissue samples.

Once an individual has been diagnosed as having pancreatic cancer, CCK A receptors become markers to monitor the patients response to treatment and prognosis. The detection of evidence of expression of CCK A receptors, e.g. protein or mRNA encoding the protein, in samples that do not normally have such evidence of expression is an important indicator of the extent and progress of the pancreatic cancer.

Tissue samples may be obtained by standard surgical techniques including use of biopsy needles. One skilled in the art would readily appreciate the variety of test samples that may be examined for CCK A receptor protein and recognize methods of obtaining tissue samples.

Tissue samples may be homogenized or otherwise prepared for screening for the presence of CCK A receptor protein by well known techniques such as sonication, mechanical disruption, chemical lysis such as detergent lysis or combinations thereof.

Examples of body fluid samples include blood, urine, lymph fluid, cerebral spinal fluid, amniotic fluid, vaginal fluid, semen and pancreatic fluid. In some preferred embodiments, blood is used as a sample of body fluid. In some preferred embodiments, pancreatic fluid is used as a sample of body fluid. Cells may be isolated from fluid sample such as centrifugation or the fluid may be analyzed without isolation of cells. In some embodiments, the cells are isolated from the fluid and the isolated cells are analyzed. In some embodiments, the fluid from which the cells were isolated is analyzed. One skilled in the art would readily appreciate the variety of test samples that may be examined for CCK A receptor protein. Test samples may be obtained by such methods as withdrawing fluid with a syringe or by a swab. In some preferred embodiments, pancreatic fluid is removed by ERCP. One skilled in the art would readily recognize other methods of obtaining test samples.

In an assay using a blood sample, the blood plasma may be separated from the blood cells. The blood plasma may be screened for CCK A receptor protein including truncated protein which is released into the blood when the CCK A receptor protein is cleaved from or sloughed off from pancreatic cancer cells. In some embodiments, blood cell fractions are screened for the presence of metastasized pancreatic cells. In some embodiments, lymphocytes present in the blood cell fraction are screened by lysing the cells and detecting the presence of CCK A receptor protein or mRNA encoding CCK A receptor protein which may be present as a result of the presence of any metastasized pancreatic cancer cells that may have been engulfed by the blood cell. In some embodiments, blood samples are analyzed to detect the presence of mRNA encoding CCK A receptor protein.

Immunoassay methods may be used to identify individuals with pancreatic cancer by detecting presence of CCK A receptor protein in sample of pancreatic tissue or other tissue or body fluid that does not normally contain CCK A receptors. The immunoassays employ antibodies which are produced in response to exposure to CCK A receptor protein and which wither do not cross react with CCK B receptors or that cross react with CCK B receptors at detectably lower levels.

The CCK A receptor specific antibodies may be polyclonal antibodies and are preferably monoclonal antibodies. The antibodies are preferably raised against CCK A receptor protein made in human cells. The antibodies preferably bind to an epitope on the extracellular domain of CCK A receptor protein. Immunoassays are well known and there design may be routinely undertaken by those having ordinary skill in the art. Those having ordinary skill in the art can produce CCK A receptor specific monoclonal antibodies which are useful in methods and kits of the invention using standard techniques and readily available starting materials. The techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which is incorporated herein by reference, provide detailed guidance for the production of hybridomas and monoclonal antibodies which specifically bind to target proteins. It is within the scope of the present invention to include FAbs and F(Ab)2s which specifically bind to CCK A receptor in place of antibodies.

Briefly, the CCK A receptor protein is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to preferentially bind to the CCK A receptor protein relative to CCK B receptors, the hybridoma which produces them is cultured to produce a continuous supply of anti-CCK A receptor protein specific antibodies.

The present invention relates to anti-CCK A receptor specific antibodies. The antibodies are preferably monoclonal antibodies. The antibodies are preferably raised against CCK A receptor protein made in human cells. In some embodiments, antibodies specifically bind to the extracellular domain of CCK A receptor protein. In some embodiments, antibodies specifically bind to the transmembrane domain. In some embodiments, antibodies specifically bind to the cytoplasmic domain.

The means to detect the presence of a protein in a test sample are routine and one having ordinary skill in the art can detect the presence or absence of CCK A receptor protein using well known methods. One well known method of detecting the presence of a protein is an immunoassay. One having ordinary skill in the art can readily appreciate the multitude of ways to practice an immunoassay to detect the presence of CCK A receptor protein in a sample.

According to some embodiments, immunoassays comprise allowing proteins in the sample to bind a solid phase support such as a plastic surface. Detectable antibodies are then added which selectively bind to the CCK A receptor protein. Detection of the detectable antibody indicates the presence of CCK A receptor protein. The detectable antibody may be a labeled or an unlabeled antibody. Unlabeled antibody may be detected using a second, labeled antibody that specifically binds to the first antibody or a second, unlabeled antibody which can be detected using labeled protein A, a protein that complexes with antibodies. Various immunoassay procedures are described in *Immunoassays for the 80's*, A. Voller et al., Eds., University Park, 1981, which is incorporated herein by reference. Controls include samples free of CCK A receptors, samples which contain CCK A receptors, and/or if the anti-CCK A receptor antibody has some cross-reactivity with the CCK 1B receptor, samples which contain CCK B receptors.

Simple immunoassays may be performed in which a solid phase support is contacted with the test sample. Any proteins present in the test sample bind the solid phase support and can be detected by a specific, detectable antibody preparation. Such a technique is the essence of the dot blot, Western blot and other such similar assays.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, *Radioimmune Assay Method*, Kirkham, Ed., E. & S. Livingstone., Edinburgh, 1970, pp. 199–206, which is incorporated herein by reference.

Other types of immunometric assays are the co-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of CCK A receptor in a test sample is anti-CCK A receptor specific antibody. By "solid phase support" or "support" is intended any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the presence of CCK A receptor protein, detectable anti-CCK A receptor specific antibodies are used. Several methods are well known for the detection of antibodies.

One method in which the antibodies can be detectably labeled is by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alphaglycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detectably labeled is through radioactive isotopes and subsequent use in a radioimmunoassay (RIA) (see, for example, Work, T. S. et al., *Laboratory Techniques and Biochemistry in Molecular Biology*, North Holland Publishing Company, N.Y., 1978, which is incorporated herein by reference). The radioactive isotope can be detected by such means as the use of a gamma counter or a scintillation counter or by autoradiography. Isotopes which are particularly useful for the purpose of the present invention are $^3$H, 125I, $^{131}$I, $^{35}$S, and $^{14}$C. Preferably $^{125}$I is the isotope. One skilled in the art would readily recognize other radioisotopes which may also be used.

It is also possible to label the antibody with a fluorescent compound. When the fluorescent-labeled antibody is exposed to light of the proper wave length, its presence can be detected due to its fluorescence. Among the most commonly used fluorescent labeling compounds are fluorescein isothiocyanate, rhodamine, phycoerythrin, phycocyanin, allophycocyanin, o-phthaldehyde and fluorescamine. One skilled in the art would readily recognize other fluorescent compounds which may also be used.

Antibodies can also be detectably labeled using fluorescence-emitting metals such as $^{152}$Eu, or others of the lanthanide series. These metals can be attached to the protein-specific antibody using such metal chelating groups as diethylenetriaminepentaacetic acid (DTPA) or ethylenediamine-tetraacetic acid (EDTA). One skilled in the art would readily recognize other fluorescence-emitting metals as well as other metal chelating groups which may also be used.

Antibody can also be detectably labeled by coupling to a chemiluminescent compound. The presence of the chemiluminescent-labeled antibody is determined by detecting the presence of luminescence that arises during the course of a chemical reaction. Examples of particularly useful chemoluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of CCK A receptor protein and no CCK A receptor protein, respectively, are added to assays being performed in parallel with the test assay. Additional controls can include a sample in a parallel assays which contains the CCK B receptor protein. One skilled in the art would have the necessary knowledge to perform the appropriate controls.

CCK A receptor protein may be produced as a reagent for positive controls routinely. One skilled in the art would appreciate the different manners in which the CCK A receptor protein may be produced and isolated.

An "antibody composition" refers to the antibody or antibodies required for the detection of the protein. For example, the antibody composition used for the detection of CCK A receptor in a test sample comprises a first antibody that binds CCK A receptor protein as well as a second or third detectable antibody that binds the first or second antibody, respectively.

To examine a test sample for the presence of CCK A receptor protein, a standard immunometric assay such as the one described below may be performed. A first anti-CCK A receptor specific antibody, which recognizes a specific portion of CCK A receptor such as the extracellular or cytoplasmic portion, is added to a 96-well microtiter plate in a volume of buffer. The plate is incubated for a period of time sufficient for binding to occur and subsequently washed with PBS to remove unbound antibody. The plate is then blocked with a PBS/BSA solution to prevent sample proteins from non-specifically binding the microtiter plate. Test sample are subsequently added to the wells and the plate is incubated for a period of time sufficient for binding to occur. The wells are washed with PBS to remove unbound protein. Labeled anti-CCK A receptor specific antibodies, which recognize portions of CCK A receptor not recognized by the first antibody, are added to the wells. The plate is incubated for a period of time sufficient for binding to occur and subsequently washed with PBS to remove unbound, labeled anti-ST receptor antibody. The amount of labeled and bound anti-CCK A receptor specific antibody is subsequently determined by standard techniques. In such an assay, one of the two antibodies used may cross react with CCK B receptors However, in preferred embodiments, the antibodies preferentially bind to CCK A receptor protein.

Kits which are useful for the detection of CCK A receptor in a test sample comprise a container comprising anti-CCK A receptor specific antibodies and instructions for performing the assays. An additional container or containers comprising controls may be provided. Such containers with controls may include sample with CCK A protein, a sample free of CCK A protein or a sample of CCK B receptor protein. The anti-CCK A receptor specific antibodies used in the kit are detectable such as being detectably labeled. If the detectable anti-CCK A receptor specific antibody is not labeled and/or requires one or more additional components for detection such as a second antibody or protein A for example, containers with such additional components may be provided in some kits in separate containers. Additional components in some kits include solid support, buffer, and photographs or illustrations of representative results. The anti-CCK A receptor specific antibodies used in the kit preferably bind to an epitope on the extracellular domain of the CCK A receptor protein. In some embodiments, the kits additionally comprise anti-CCK B receptor specific antibodies.

The immunoassay is useful for detecting free or cell bound CCK A receptor in homogenized tissue samples and body fluid samples including the plasma portion or cells in the fluid sample.

Western Blots may be used in methods of identifying individuals suffering from pancreatic cancer by detecting presence of CCK A receptor protein in sample of tissue or body fluid normally free of such CCK A receptors. Western blots may also be used to detect presence of CCK A receptor protein in sample of tumor from an individual suffering from cancer to identify and/or confirm that the tumor is pancreatic in origin. Western blots use detectable anti-CCK A receptor specific antibodies to bind to any CCK A receptor present in a sample and thus indicate the presence of the receptor in the sample.

Western blot techniques, which are described in Sambrook, J. et al., (1989) *Molecular Cloning: A Laboratory Manual*, Cold Spring Harbor Laboratory Press, Cold Spring Harbor, N.Y., which is incorporated herein by reference, are similar to immunoassays with the essential difference being that prior to exposing the sample to the antibodies, the proteins in the samples are separated by gel electrophoresis and the separated proteins are then probed with antibodies. In some preferred embodiments, the matrix is an SDS-PAGE gel matrix and the separated proteins in the matrix are transferred to a carrier such as filter paper prior to probing with antibodies. Anti-CCK A receptor specific antibodies described above are useful in Western blot methods.

Generally, samples are homogenized and cells are lysed using detergent such as Triton-X. The material is then separated by the standard techniques in Sambrook, J. et al., (1989) *Molecular Cloning: A Laboratory Manual*, Cold Spring Harbor Laboratory Press, Cold Spring Harbor, N.Y.

Kits which are useful for the detection of CCK A receptor in a test sample by Western Blot comprise a container comprising anti-CCK A receptor specific antibodies and instructions for performing the assays. An additional container or containers comprising controls may be provided. Such containers with controls may include a sample with CCK A protein, a sample free of CCK A protein or a sample of CCK B receptor protein. The anti-CCK A receptor specific antibodies used in the kit are detectable such as being detectably labeled. If the detectable anti-CCK A receptor specific antibody is not labeled and/or requires one or more additional components for detection such as a second antibody or protein A for example, containers with such additional components may be provided in some kits in separate containers. Additional components in some kits include size markers, buffer, and photographs or illustrations of representative results. The anti-CCK A receptor specific antibodies used in the kit preferably bind to an epitope on the extracellular domain of the CCK A receptor protein. In some embodiments, a container comprising anti-CCK B receptor specific antibodies is provided.

Western blots are useful for detecting CCK A receptor in homogenized tissue samples and body fluid samples including the plasma portion or cells in the fluid sample.

CCK A receptor specific ligand binding assays may be used in methods of identifying individuals suffering from pancreatic cancer by detecting presence of CCK A receptor protein in sample of tissue or body fluid. CCK A receptor specific ligand binding assays may also be used in methods to detect presence of CCK A receptor protein in sample of tumor from an individual suffering from cancer to identify and/or confirm that the tumor is pancreatic in origin. The CCK A receptor specific ligand binding assay uses a detectable CCK A receptor specific ligand to bind to any CCK A receptor present and thus indicate the presence of the receptor in a sample. CCK A receptor ligands are described above. Such ligands may be used in ligand binding assays to detect the presence of CCK A receptors in a sample.

The CCK A receptor specific ligand binding assay, described above, can be readily performed by those having ordinary skill in the art using readily available starting materials. CCK A receptor specific ligand binding assays may be performed a variety of ways but each essentially identify whether or not a CCK A receptor protein is present in a sample by determining whether or not a detectable CCK A receptor specific ligand binds to a receptor in a sample. Briefly, the assay consists of incubating a sample with a constant concentration of a CCK A receptor specific ligand. As a control, a duplicate preparation of a sample known to contain CCK A receptors are incubated with a duplicate concentration of ligand. Assays are incubated to equilibrium (for example 2 hours) and the sample is analyzed to determine whether or not ligand is bound to material in the sample. The ligand/sample is passed through a filter which is capable of allowing ligand to pass through but not capable of allowing CCK A receptor to pass through. Thus, if CCK A receptor is present in the sample, it will bind the ligand which will then be trapped by the filter. Detection of ligand in the filter indicates the presence of CCK A receptor in the sample. In some preferred embodiments, the filter is Whitman GFB glass filter paper. Controls include using samples which are known to contain CCK A receptors.

If the sample being tested is from tissue or fluid which does not normally contain CCK B receptors, the ligand used can bind to CCK B receptors as well. Such ligands include CCK itself.

Kits include containers comprising detectable CCK A receptor ligand together with and instructions for performing the assays. An additional container or containers comprising controls may be provided. Such containers with controls may include a sample with CCK A protein, a sample free of CCK A protein or a sample of CCK B receptor protein. The anti-CCK A receptor ligand used in the kit are detectable such as being detectably labeled. If the detectable CCK A receptor ligand is not labeled and/or requires one or more additional components for detection such as an antibody for example, containers with such additional components may be provided in some kits in separate containers. Additional components in some kits include solid support or filter, buffer, and photographs or illustrations of representative results. The detectable CCK A receptor ligand is preferably labeled. The detectable CCK A receptor ligand is preferably radiolabeled, preferably radiolabeled with .25I.

The CCK A receptor binding assay is useful for detecting CCK A receptor in homogenized tissue samples and body fluid samples including the plasma portion or cells in the fluid sample.

In addition to detection of the CCK A receptor protein, aspects of the present invention include various methods of determining whether a sample contains cells that express CCK A receptor by nucleotide sequence-based molecular analysis. Several different methods are available for doing so including those using Polymerase Chain Reaction (PCR) technology, branched chain oligonucleotide hybridization technology, Northern blot technology, oligonucleotide hybridization technology, and in situ hybridization technology. The invention relates to oligonucleotide probes and primers used in the methods of identifying mRNA that encodes CCK A receptor and to diagnostic kits which comprise such components. The mRNA sequence-based methods for determining whether a sample mRNA encoding CCK A receptor include but are not limited to polymerase chain reaction technology, branched chain oligonucleotide hybridization technology, Northern and Southern blot technology, in situ hybridization technology and oligonucleotide hybridization technology.

The methods described herein are meant to exemplify how the present invention may be practiced and are not meant to limit the scope of invention. It is contemplated that other sequence-based methodology for detecting the presence of specific mRNA that encodes CCK A receptor samples may be employed according to the invention.

A preferred method to detecting mRNA that encodes CCK A receptor in genetic material derived from samples that: do not normally express CCK A receptors uses polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. U.S. Pat. No. 4,683,202, U.S. Pat. No. 4,683,195, U.S. Pat. No. 4,965,188 and U.S. Pat. No. 5,075,216, which are each incorporated herein by reference describe methods of performing PCR. PCR may be routinely practiced using Perkin Elmer Cetus GENE AMP RNA PCR kit, Part No. N808-0017.

PCR technology including RT-PCR allows for the rapid generation of multiple copies of DNA sequences by providing sets of primers that hybridize to sequences present in an RNA or DNA molecule, and further providing free nucleotides and an enzyme which fills in the complementary bases to the nucleotide sequence adjacent to and thereby between the primers with the free nucleotides to produce a complementary strands of DNA. The enzyme will fill in the complementary sequences adjacent to the primers. If both of the primers hybridize to nucleotide sequences on the same small fragment of nucleic acid, exponential amplification of a specific double-stranded size product results. If only a single primer hybridizes to the nucleic acid fragment, linear amplification produces single-stranded products of variable length.

PCR primers can be designed routinely by those having ordinary skill in the art using sequence information. The nucleotide sequence encoding CCK A receptor protein is well known such as in Wank S. A., et al. 1994 *Annal NY Acad Sci* 713:49–66, which is incorporated herein by reference as are all references referred to therein. The nucleotide sequence that encodes the CCK B receptor, also disclosed therein, may be used to design primers which specifically amplify mRNA that encodes CCK A receptor protein. To perform this method, RNA is extracted from cells in a sample and tested or used to make cDNA using well known methods and readily available starting materials.

Those having ordinary skill in the art can readily prepare PCR primers. A set of primers generally contains two primers. When performing PCR on extracted mRNA or cDNA generated therefrom, if the mRNA or cDNA encoding CCK A receptor protein is present, multiple copies of the mRNA or cDNA will be made. If it is not present, PCR will not generate a discrete detectable product. Primers are generally 8–50 nucleotides, preferably about 15–35 nucleotides, more preferably 18–28 nucleotides, which are identical or complementary to and therefor hybridize to the mRNA or cDNA generated therefrom which encodes CCK A receptor protein. In preferred embodiments, the primers are each 15–35 nucleotide, more preferably 18–28 nucleotide fragments of the nucleic acid molecule that comprises the nucleotide sequence encoding CCK A receptor protein. The primer must hybridize to the sequence to be amplified. Typical primers are 18–28 nucleotides in length and are generally have 50% to 60% G+C composition. The entire primer is preferably complementary to the sequence it must hybridize to. Preferably, primers generate PCR products 100 base pairs to 2000 base pairs. However, it is possible to generate products of 50 to up to 10 kb and more. If mRNA is used as a template, the primers must hybridize to mRNA sequences. If cDNA is used as a template, the primers must hybridize to cDNA sequences. The extracellular domain is the most unique portion of the CCK A receptor protein. At least one primer hybridizes to a nucleotide sequence that corresponds to the extracellular domain of the CCK A receptor protein.

The mRNA or cDNA is combined with the primers, free nucleotides and enzyme following standard PCR protocols. The mixture undergoes a series of temperature changes. If the mRNA or cDNA encoding CCK A receptor is present, that is, if both primers hybridize to sequences, the molecule comprising the primers and the intervening complementary sequences will be exponentially amplified. The amplified DNA can be easily detected by a variety of well known means. If no mRNA or cDNA that encodes CCK A receptor is present, no PCR product will be exponentially amplified. The PCR technology therefore provides an extremely easy, straightforward and reliable method of detecting mRNA encoding CCK A receptor protein in a sample.

PCR product may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize between sequences hybridized to by the first set of primers.

The present invention includes oligonucleotide which are useful as primers for performing PCR methods to amplify mRNA or cDNA that encodes CCK A receptor protein.

According to the invention, diagnostic kits can be assembled which are useful to practice methods of detecting the presence of mRNA or cDNA that encodes CCK A receptor in samples. Such diagnostic kits comprise a container with oligonucleotides that are useful as primers for performing PCR methods and instructions for performing the assay. It is preferred that diagnostic kits according to the present invention comprise a container comprising a size marker to be run as a standard on a gel used to detect the presence of amplified DNA. The size marker is the same size as the DNA generated by the primers in the presence of the mRNA or cDNA encoding CCK A receptor. Optionally, another container may be provided which contains a positive control, i.e. a nucleic acid molecule which includes the CCK A receptor-encoding sequences to be amplified by the PCR primers. Similarly, the kit may optionally comprise another container which contains a negative control, i.e. a nucleic acid molecule which does not includes the CCK A receptor-encoding sequences to be amplified by the PCR primers. Additional items in some kits include photographs or illustrations of representative results.

PCR assays are useful for detecting mRNA encoding CCK A receptor in homogenized tissue samples and cells in body fluid samples. It is contemplated that PCR on the plasma portion of a fluid sample could be used to detect mRNA encoding CCK A receptor protein.

Another method of determining whether a sample contains cells expressing CCK A receptor is by branched chain oligonucleotide hybridization analysis of mRNA extracted from a sample. Branched chain oligonucleotide hybridization may be performed as described in U.S. Pat. No. 5,597,909, U.S. Pat. No. 5,437,977 and U.S. Pat. No. 5,430,138, which are each incorporated herein by reference. Reagents may be designed following the teachings of those patents and that sequence of the CCK A mRNA.

Another method of determining whether a sample contains cells expressing CCK A receptor is by Northern Blot analysis of mRNA extracted from a sample. The techniques for performing Northern blot analyses are well known by those having ordinary skill in the art and are described in Sambrook, J. et al., (1989) *Molecular Cloning: A Laboratory Manual*, Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

The mRNA is extracted using poly dT columns and the material is separated by electrophoresis and, for example, transferred to nitrocellulose paper. Labeled probes made from an isolated specific fragment or fragments can be used to visualize the presence of a complementary fragment fixed to the paper. Probes useful to identify mRNA in a Northern Blot have a nucleotide sequence that is complementary to mRNA transcribed from the gene that encodes CCK A receptor protein. Those having ordinary skill in the art could design such probes or to isolate and clone the CCK A receptor gene or cDNA which can be used as a probe. Probes preferably hybridize to the portion of the mRNA that corresponds to the extracellular domain of the CCK receptor protein. In preferred embodiments, the probes are full length clones or fragments of the nucleic acid molecule that comprises the nucleotide sequence encoding CCK A receptor protein. Such probes are at least 15 nucleotides, preferably 30–200, more preferably 40–100 nucleotide fragments and may be the entire coding sequence of CCK A receptors, more preferably 18–28 nucleotide fragments of the nucleic acid molecule that comprises the nucleotide sequence encoding CCK A receptor protein. A preferred probe hybridizes to the mRNA that encodes CCK A receptor protein from nucleotide 50 to nucleotide 90.

According to the invention, diagnostic kits can be assembled which are useful to practice methods of detecting the presence of mRNA that encodes CCK A receptor in samples by Northern blot analysis. Such diagnostic kits comprise oligonucleotide which are useful as probes for hybridizing to the mRNA and instructions for performing the assay. The probes may be radiolabeled. It is preferred that diagnostic kits according to the present invention comprise a container comprising a size marker to be run as a standard on a gel. It is preferred that diagnostic kits according to the present invention comprise a container comprising a positive control which will hybridize to the probe, e.g. a nucleic acid molecule which includes the CCK A receptor-encoding sequences. Similarly, the kit may optionally comprise another container which contains a negative control, i.e. a nucleic acid molecule which does not includes the CCK A receptor-encoding sequences. Additional items in some kits include photographs or illustrations of representative results.

Northern blot analysis is useful for detecting mRNA encoding CCK A receptor in homogenized tissue samples and cells in body fluid samples. It is contemplated that Northern Blot analysis on the plasma portion of a fluid sample could be used to detect mRNA encoding CCK A receptor protein.

Another method of detecting the presence of mRNA encoding CCK A receptor protein by oligonucleotide hybridization technology. Oligonucleotide hybridization technology is well known to those having ordinary skill in the art. Briefly, detectable probes which contain a specific nucleotide sequence that will hybridize to nucleotide sequence of mRNA encoding CCK A receptor protein. RNA or cDNA made from RNA from a sample is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences.

Probes useful in oligonucleotide assays at least 18 nucleotides of complementary DNA and may be as large as a complete complementary sequence to CCK A receptor cDNA. In some preferred embodiments the probes of the invention are 30–200 nucleotides, preferably 40–100 nucleotides. The probes preferably contain a sequence that is complementary to the portion that encodes the extracellular domain of the CCK A receptor.

One having ordinary skill in the art can design probes which are fully complementary to CCK A mRNA sequences but not genomic DNA sequences or CCK B sequences. Hybridization conditions can be routinely optimized to minimize background signal by non-fully complementary hybridization. Probes preferably hybridize to the portion of the mRNA that includes a nucleotide sequence that corresponds to the extracellular domain of the CCK A receptor protein. Probes preferably hybridize to the portion of the mRNA that corresponds to the extracellular domain of the CCK A receptor protein. In preferred embodiments, the probes are full length clones or fragments of the nucleic acid molecule that comprises the nucleotide sequence encoding CCK A receptor protein. Such probes are at least 15 nucleotides, preferably 30–200, more preferably 40–100 nucleotide fragments and may be the entire coding sequence of CCK A receptors, more preferably 18–28 nucleotide fragments of the nucleic acid molecule that comprises the nucleotide sequence encoding CCK A receptor protein. A preferred probe hybridizes to the mRNA that encodes CCK A receptor protein from nucleotide 50 to nucleotide 90.

The present invention includes labeled oligonucleotide which are useful as probes for performing oligonucleotide hybridization. That is, they are fully complementary with mRNA sequences but not genomic sequences. For example, the mRNA sequence includes portions encoded by different exons. The labeled probes of the present invention are labeled with radiolabeled nucleotides or are otherwise detectable by readily available nonradioactive detection systems.

According to the invention, diagnostic kits can be assembled which are useful to practice oligonucleotide hybridization methods of the invention. Such diagnostic kits comprise a labeled oligonucleotide which encodes portions of CCK A receptor encoded by different exons and instructions for performing the assay. It is preferred that labeled probes of the oligonucleotide diagnostic kits according to the present invention are labeled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Additional items in some kits include photographs or illustrations of representative results. Under assay conditions, the probe will not hybridize to the negative control DNA sample. Those having ordinary skill in the art could design such probes or to isolate and clone the CCK A receptor gene or cDNA which can be used as a probe. Either the coding strand or its complementary strand may be used as a probe.

Oligonucleotide hybridization techniques are useful for detecting mRNA encoding CCK A receptor in homogenized tissue samples and cells in body fluid samples. It is contemplated that oligonucleotide hybridization will be useful to detect mRNA encoding CCK A receptor protein in the plasma portion of a fluid sample.

The present invention relates to in vitro kits for evaluating samples of tumors to determine whether or not they are pancreatic in origin and to reagents and compositions useful to practice the same. In some embodiments of the invention, tumor samples may be isolated from individuals undergoing or recovery from surgery to remove tumors in the pancreas, tumors in other organs or biopsy material. The tumor sample is analyzed to identify the presence or absence of the CCK A receptor protein. Techniques such as a CCK A receptor/ligand binding assays and immunohistochemistry assays may be performed to determine whether the CCK A receptor is present in cells in the tumor sample which are indicative of pancreatic origin. Alternatively, in some embodiments of the invention, pancreatic tissue samples are analyzed to identify whether CCK A receptor protein is being expressed in cells sample which indicate pancreatic cancer. The presence of CCK A receptor protein or mRNA that encodes the CCK A receptor protein or cDNA generated therefrom can be determined using techniques such as in situ hybridization and immunohistochemistry.

In situ hybridization technology is well known by those having ordinary skill in the art. Briefly, cells are fixed and detectable probes which contain a specific nucleotide sequence are added to the fixed cells. If the cells contain complementary nucleotide sequences, the probes, which can be detected, will hybridize to them.

Probes useful in oligonucleotide assays at least 18 nucleotides of complementary DNA and may be as large as a complete complementary sequence to CCK A receptor mRNA. In some preferred embodiments the probes of the invention are 30–200 nucleotides, preferably 40–100 nucleotides. The probes preferably contain a sequence that is complementary to the portion that encodes the extracellular domain of the CCK A receptor.

One having ordinary skill in the art can design probes useful in in situ hybridization technology to identify cells that express CCK A receptor. Probes preferably hybridizes to a nucleotide sequence that corresponds to the extracellular domain of the CCK A receptor protein. Hybridization conditions can be routinely optimized to minimize background signal by non-fully complementary hybridization. Probes preferably hybridize to the portion of the mRNA that includes a nucleotide sequence that corresponds to the extracellular domain of the CCK A receptor protein. Probes preferably hybridize to the portion of the mRNA that corresponds to the extracellular domain of the CCK A receptor protein. In preferred embodiments, the probes are full length clones or fragments of the nucleic acid molecule that comprises the nucleotide sequence encoding CCK A receptor protein. Such probes are at least 15 nucleotides, preferably 30–200, more preferably 40–100 nucleotide fragments and may be the entire coding sequence of CCK A receptors, more preferably 18–28 nucleotide fragments of the nucleic acid molecule that comprises the nucleotide sequence encoding CCK A receptor protein.

The probes are fully complementary and do not hybridize well to partially complementary sequences. For in situ hybridization according to the invention, it is preferred that the probes are detectable by fluorescence. A common procedure is to label probe with biotin-modified nucleotide and then detect with fluorescently tagged avidin. Hence, probe does not itself have to be labeled with florescent but can be subsequently detected with florescent marker.

The present invention includes labeled oligonucleotide which are useful as probes for performing oligonucleotide hybridization. That is, they are fully complementary with mRNA sequences but not genomic sequences. For example, the mRNA sequence includes portions encoded by different exons. The labeled probes of the present invention are labeled with radiolabeled nucleotides or are otherwise detectable by readily available nonradioactive detection systems.

The present invention relates to probes useful for in situ hybridization to identify cells that express CCK A receptor protein.

Cells are fixed and the probes are added to the genetic material. Probes will hybridize to the complementary nucleic acid sequences present in the sample. Using a fluorescent microscope, the probes can be visualized by their fluorescent markers.

According to the invention, diagnostic kits can be assembled which are useful to practice in situ hybridization methods of the invention are fully complementary with mRNA sequences but not genomic sequences. For example, the mRNA sequence includes portions encoded by different exons. It is preferred that labeled probes of the in situ diagnostic kits according to the present invention are labeled with a fluorescent marker. Kits additionally contain instructions for performing the assays. Optionally, containers having positive and/or negative controls may be provided as well as photographs and illustrations of representative results.

Immunohistochemistry techniques may be used to identify and essentially stain cells with CCK A receptors. Anti- CCK A receptor specific antibodies such as those described above of contacted with fixed cells and the CCK A receptor present in the cells reacts with the antibodies. The antibodies are detectably labeled or detected using labeled second antibody or protein A to stain the cells.

The techniques described herein for evaluating tumor sections can also be used to analyze tissue sections for samples of lymph nodes or pancreatic tissue as well as other tissues to identify the presence of pancreatic cancer cells. The samples can be prepared and "stained" to detect expression of CCK A receptor.

The following examples are illustrative but are not meant to be limiting of the present invention.

EXAMPLES

Example 1

One procedure for crosslinking CCK A receptor ligands which have a free amino group to active agents which have a free amino group such as methotrexate, doxorubicin, daunorubicin, cytosinarabinoside, cis-platin, vindesine, mitomycin and bleomycin, or alkaline phosphatase, or proteinor peptide-based toxin employs homobifunctional succinimidyl esters, preferably with chain carbon spacers such as disuccinimidyl suberate (Pierce Co, Rockford, Ill.).

A CCK A binding ligand with the free amino group is incubated in the presence of the chemical crosslinking agent and an active agent which have a free amino group in equimolar quantities at room temperature for 15–30 min. Incubation is terminated by separating the reactants by gel permeation chromatography by HPLC. This technique separates the conjugated compounds from free active agents and free CCK A binding ligands, active agent-active agent conjugates and CCK A binding ligand-CCK A binding ligand conjugates. Homogeneous preparations of conjugated through their free amino groups and with a preferred molar ratio of 1:1 are obtained.

Example 2

In the event that a cleavable conjugated compound, is required, the same protocol as described above may be employed utilizing 3,3'-dithiobis (sulfosuccinimidylpropionate (SPDP); Pierce, Ill.). SPDP forms a sulfhydryl group from a free amino group which may be used to conjugate a compound to another free amino group. For example, CCK A binding peptides are derivatized using established procedures employing N-succinimidyl-3 (2-pyridildithio)-propionate (SPDP, Pharmacia-LKB, NJ). The CCK A biding peptide is incubated with a 5-fold molar excess of SPDP for 30 minutes at room temperature. The peptide-pyridylthiopropionate conjugate is separated from unreacted reagents by gel permeation chromatography by HPLC. An active agent with a free amino group, such as a protein-based toxin, is prepared for conjugation by reduction with dithiothreitol for 4 hours at room temperature. Reduced active agent is incubated with a 2-fold molar excess of CCK A receptor ligand-PDP conjugate at pH 8.0 for 36 hours at 4©C. Conjugate compound is purified from unreacted agents by gel permeation chromatography by HPLC.

This protocol for conjugation is particularly useful to conjugate CCK A binding peptides to diphtheria toxin A chains and Pseudomonas exotoxin as well as ricin toxin A chains (Magerstadt, M. *Antibody Conjugates and Malignant Disease*. (1991) CRC Press, Boca Raton, USA, pp. 110–152; Cawley, D. B. et al. (1980) *Cell* 22:563; Cumber, A. J., et al. (1985) *Meth. Enz.* 112:207; Gros, O. (1985) *J. Immunol.* *Meth.* 81:283; Worrell, N. R., et al. (1986) *Anti-Cancer Drug Design* 1:179; Thorpe, P. E. et al. (1987) *Cancer Res.* 47:5924, each of which is incorporated herein by reference).

Example 3

Active agents with a free amino group may be derivatized with SPDP as described above and conjugated with a CCK A ligand that has a free amino group and that has been modified with the succinimidyl ester of iodoacetic acid (Pierce Co., Rockford, Ill.) (Magerstadt, M. (1991) *Antibody Conjugates And Malignant Disease*, CRC Press Boca Raton; Cumber, A. J. et al. (1985) *Meth. Enz.* 112:20, which are incorporated herein by reference). Conjugation relies on the selective reaction of iodoacetyl groups introduced into the amino terminal of the CCK A ligand with the thiol groups introduced into the active agent. As with the above protocol, this procedure avoids homopolymer formation. However, the product is conjugated through a central thioether linkage which cannot be reduced.

Example 4

A CCK A receptor ligand with a free amino group and active agents with free amino groups may be conjugated through a disulfide bond using iminothiolane (Pierce, Rockford, Ill.) (Fitzgerald, D. J. P. et al. (1983) *Cell* 32:607; Magerstadt, M. (1991) *Antibody Conjugates And Malignant Disease*, CRC Press, Boca Raton; Bjorn, M. J., et al. (1985) *Cancer Res.* 45:1214; Bjorn, M. J., et al. (1986) *Cancer Res.* 46:3262, which are incorporated herein by reference). The CCK A receptor ligand with a free amino group is derivatized at the amino terminal with iminothiolane and the active agent: is derivatized with SPDP as described above. Reacting iminothiolane-derivatized CCK A receptor ligand with SPDP-derivatized active agent results in conjugation by a reducible disulfide bond. In addition, iminothiolane provides the versatility to conjugate these proteins through bonds other than disulfides. Thus, derivatization of active agents with the heterobifunctional agent sulfosuccinimidyl 4-(N-maleimidomethyl) cyclohexane (Pierce, Rockford, Ill.) and reaction with iminothiolane-derivatized CCK A receptor ligand will conjugate these peptides without formation of disulfides.

Example 5

As stated above, a CCK A receptor specific binding moiety is a CCK A receptor ligand that may be a peptide or a non-peptide. Peptides and non-peptide CCK A receptor specific ligands may be identified using well known technology such as combinatorial library technology.

Over the past 10 years, it has become recognized that the specific high-affinity interaction of a receptor and its ligand, for example CCK A receptor and CCK, has its basis in the 3-dimensional conformational space of the ligand and the complimentary 3-dimensional configuration of the region of the receptor molecule involved in ligand binding (the receptor boding pocket). In addition, it has become recognized that various arrays of naturally-occurring amino acids, non-natural amino acids, and organic molecules can be organized in configurations that are unrelated to the natural ligands in their linear structure, but resemble the 3-dimensional structure of the natural ligands in conformational space and, thus, are recognized by receptors with high affinity and specificity. Furthermore, techniques have been described in the literature that permit one of ordinary skill in the art to generate large libraries of these arrays of natural amino acids, non-natural amino acids and organic compounds to prospectively identify individual compounds that interact with receptors with high affinity and specificity which are unrelated to the native ligand of that receptor. Thus, it is a relatively straightforward task for one of ordinary skill in the art to identify arrays of naturally occurring amino acids, non-natural amino acids, or organic compounds which can bind specifically and tightly to the CCK A receptor, which bear no structural relationship to CCK.

To identify CCK A receptor ligands that are peptides, those having ordinary skill in the art can use any of the well known methodologies for screening random peptide libraries in order to identify peptides which bind to the CCK A receptor. In the most basic of methodologies, the peptides which bind to the target are isolated and sequenced. In some methodologies, each random peptide is linked to a nucleic acid molecule which includes the coding sequence for that particular random peptide. The random peptides, each with an attached coding sequence, are contacted with the CCK A receptor and the peptides which are unbound to the CCK A receptor are removed. The nucleic acid molecule which includes the coding sequence of the peptide that binds to the CCK A receptor can then be used to determine the amino acid sequence of the peptide as well as produce large quantities of the peptide. It is also possible to produce peptide libraries on solid supports where the spatial location on the support corresponds to a specific synthesis and therefore specific peptide. Such methods often use photolithography-like steps to create diverse peptide libraries on solid supports in which the spatial address on the support allows for the determination of the sequence.

The production of organic compound libraries on solid supports may also be used to produce combinatorial libraries of non-peptide compounds such as oligonucleotides and sugars, for example. As in the case of peptide libraries on solid supports, the spatial location on the support corresponds to a specific synthesis and therefore specific compound. Such methods often use photolithography-like steps to create diverse compound libraries on solid supports in which the spatial address on the support allows for the determination of the synthesis scheme which produced the compound. Once the synthesis scheme is identified, the structure of the compound can become known.

Gallop et al. 1994 *J. Medicinal Chemistry* 37:1233, which is incorporated herein by reference, provides a review of several of the various methodologies of screening random peptide libraries and identifying peptides from such libraries which bind to target proteins. Following these teachings, CCK A receptor specific ligands that are peptides and that are useful as CCK A receptor specific binding moieties may be identified by those having ordinary skill in the art.

Peptides and proteins displayed on phage particles are described in Gallop et al. Supra. Random arrays of nucleic acids can be inserted into genes encoding surface proteins of bacteriophage which are employed to infect bacteria, yielding phage expressing the peptides encoded by the random array of nucleotides on their surface. These phage displaying the peptide can be employed to determine whether those peptides can bind to specific proteins, receptors, antibodies, etc. The identity of the peptide can be determined by sequencing the recombinant DNA from the phage expressing the peptide. This approach has the potential to yield vast arrays of peptides in a library (up to $10^9$ unique peptides). This technique has been employed to identify novel binding peptides to the fibrinogen receptor on platelets, which bear no sequence homology to the natural occurring ligands of this receptor (Smith et al., 1993 *Gene* 128:37, which is incorporated herein by reference). Similarly, this technique has been applied to identify peptides which bind to the MHC class II receptor (Hammer et al., 1993 *Cell* 74:197, which is incorporated herein by reference) and the chaperonin receptor (Blond-Elguindi et al., 1993 *Cell* 75:717, which is incorporated herein by reference).

Peptides displayed on plasmids are described in Gallop et al. Supra. In this approach, the random oligonucleotides which encode the library of peptides can be expressed on a specific plasmid whose expression is under the control of a specific promoter, such as the lac operon. The peptides are expressed as fusion proteins coupled to the Lac I protein, under the control of the lac operon. The fusion protein specifically binds to the lac operator on the plasmid and so the random peptide is associated with the specific DNA element that encodes it. In this way, the sequence of the peptide can be deduced, by PCR of the DNA associated with the fusion protein. These proteins can be screened in solution phase to determine whether they bind to specific receptors. Employing this approach, novel substrates have been identified for specific enzymes (Schatz 1993).

A variation of the above technique, also described in Gallop et al. Supra, can be employed in which random oligonucleotides encoding peptide libraries on plasmids can be expressed in cell-free systems. In this approach, a molecular DNA library can be constructed containing the random array of oligonucleotides, which are then expressed in a bacterial in vitro transcription/translation system. The identity of the ligand is determined by purifying the complex of nascent chain peptide/polysome containing the mRNA of interest on affinity resins composed of the receptor and then sequencing following amplification with RT-PCR. Employing this technique permits generation of large libraries (up to $10^{11}$ recombinants). Peptides which recognize antibodies specifically directed to dynorphin have been identified employing this technique (Cull et al., 1992 *Proc. Natl. Acad. Sci. USA* 89:1865, which is incorporated herein by reference).

Libraries of peptides can be generated for screening against a receptor by chemical synthesis. For example, simultaneous preparation of large numbers of diverse peptides have been generated employing the approach of multiple peptide synthesis as described in Gallop et al. Supra. In one application, random peptides are generated by standard solid-phase Merrifield synthesis on polyacrylamide microtiter plates (multipin synthesis) which are subsequently screened for their ability to compete with receptor binding in a standard competitive binding assay (Wang et al., 1993 *Bioorg. Med. Chem. Lett.* 3:447, which is incorporated herein by reference). Indeed, this approach has been employed to identify novel binding peptides to the substance P receptor (Wang et al. Supra). Similarly, peptide libraries can be constructed by multiple peptide synthesis employing the "tea bag" method in which bags of solid support resin are sequentially incubated with various amino acids to generate arrays of different peptides (Gallop et al. Supra). Employing this approach, peptides which bind to the integrin receptor (Ruggeri et al., 1986 *Proc. Natl. Acad. Sci. USA* 83:5708, which is incorporated herein by reference) and the neuropeptide Y receptor (Beck-Sickinger et al., 1990 *Int. J. Peptide Protein Res.* 36:522, which is incorporated herein by reference) have been identified.

In general, the generation and utility of combinatorial libraries depend on (1) a method to generate diverse arrays of building blocks, (2) a method for identifying members of the array that yield the desired function, and (3) a method for deconvoluting the structure of that member. Several approaches to these constraints have been defined.

The following is a description of methods of library generation which can be used in procedures for identifying CCK A receptor specific ligands according to the invention.

Modifications of the above approaches can be employed to generate libraries of vast molecular diversity by connecting together members of a set of chemical building blocks, such as amino acids, in all possible combinations (Gallop et al. Supra) In one approach, mixtures of activated monomers are coupled to a growing chain of amino acids on a solid support at each cycle. This is a multivalent synthetic system.

Also, split synthesis involves incubating the growing chain in individual reactions containing only a single building block (Gallop et al. Supra). Following attachment, resin from all the reactions are mixed and apportioned into individual reactions for the next step of coupling. These approaches yield a stochastic collection of $n^x$ different peptides for screening, where n is the number of building blocks and x is the number of cycles of reaction.

Alternatively, arrays of molecules can be generated in which one or more positions contain known amino acids, while the remainder are random (Gallop et al. Supra). These yield a limited library which is screened for members with the desired activity. These members are identified, their structure determined, and the structure regenerated with another position containing defined amino acids and screened. This iterative approach ultimately yields peptides which are optimal for recognizing the conformational binding pocket of a receptor.

In addition, arrays are not limited to amino acids forming peptides, but can be extended to linear and nonlinear arrays of organic molecules (Gordon et al., 1994 *J. Medicinal Chemistry* 37:1385, which is incorporated herein by reference). Indeed, employing this approach of generating libraries of randomly arrayed inorganic building blocks, ligands which bound to 7-transmembrane receptors were identified (Zuckermann et al., 1994 *J. Med. Chem.* 37:2678, which is incorporated herein by reference).

Libraries are currently being constructed which can be modified after synthesis to alter the chemical side groups and bonds, to give "designer" arrays to test for their interaction with receptors (Osteresh et al., 1994 *Proc. Natl. Acad. Sci. USA* 91:11138, which is incorporated herein by reference). This technique, generating "libraries from libraries", was applied to the permethylation of a peptide library which yielded compounds with selective antimicrobial activity against gram positive bacteria.

Libraries are also being constructed to express arrays of pharmacological motifs, rather than specific structural arrays of amino acids (Sepetov et al., 1995 *Proc. Natl. Acad. Sci. USA* 92:5426, which is incorporated herein by reference). This technique seeks to identify structural motifs that have specific affinities for receptors, which can be modified in further refinements employing libraries to define structure-activity relationships. Employing this approach of searching motif libraries, generating "libraries of libraries", reduces the number of component members required for screening in the early phase of library examination.

The following is a description of methods of identifying CCK A receptor specific ligands according to the invention from libraries of randomly generated molecules.

Components in the library which interact with receptors may be identified by their binding to receptors immobilized on solid support (Gordon et al. Supra).

They may also be identified by their ability to compete with native ligand for binding to cognate receptors in solution phase (Gordon et al. Supra).

Components may be identified by their binding to soluble receptors when those components are immobilized on solid supports (Gordon et al. Supra).

Once a member of a library which binds receptors has been identified, the structure of that member must be deconvoluted (deduced) in order to identify the structure and generate large quantities to work with, or develop further analogs to study structure-activity relationships. The following is a description of methods of deconvolution for deducing the structure of molecules identified as potential CCK A receptor specific ligands according to the invention.

Peptide libraries may be expressed on the surface of bacteriophage particles (Gallop et al. Supra). Once the peptide interacting with the receptor has been identified, its structure can be deduced by isolating the DNA from the phage and determining its sequence by PCR.

Libraries expressed on plasmids, under the control of the Lac operon can be deconvoluted since these peptides are fused with the lac I protein which specifically interacts with the lac operon on the plasmid encoding the peptide (Gallop et al. Supra) The structure can be deduced by isolating that plasmid attached to the lac I protein and deducing the nucleotide and peptide sequence by PCR.

Libraries expressed on plasmids can also be expressed in cell-free systems employing transcription/translation systems (Gallop et al. Supra). In this paradigm, the protein interacting with receptors is isolated with its attached ribosome and mRNA. The sequence of the peptide is deduced by RT-PCR of the associated mRNA.

Library construction can be coupled with photolithography, so that the structure of any member of the library can be deduced by determining its position within the substrate array (Gallop et al. Supra). This technique is termed positional addressability, since the structural information can be deduced by the precise position of the member.

Members of a library can also be identified by tagging the library with identifiable arrays of other molecules (Ohlmeyer et al., 1993 *Proc. Natl. Acad. Sci. USA* 90:10922, which is incorporated herein by reference, and Gallop et al. Supra). This technique is a modification of associating the peptide with the plasmid of phage encoding the sequence, described above. Some methods employ arrays of nucleotides to encode the sequential synthetic history of the peptide. Thus, nucleotides are attached to the growing peptide sequentially, and can be decoded by PCR to yield the structure of the associated peptide. Alternatively, arrays of small organic molecules can be employed as sequencable tags which encode the sequential synthetic history of the peptide. Thus, nucleotides are attached to the growing peptide sequentially, and can be decoded by PCR to yield the structure of the associated peptide. Alternatively, arrays of small organic molecules can be employed as sequencable tags which encode the sequential synthetic history of the library member.

Finally, the structure of a member of the library can be directly determined by amino acid sequence analysis.

The following patents, which are each incorporated herein by reference, describe methods of making random peptide or non-peptide libraries and screening such libraries to identify compounds that bind to target proteins. As used in the present invention, CCK A receptors can be the targets used to identify the peptide and non-peptide ligands generated and screened as disclosed in the patents.

U.S. Pat. No. 5,270,170 issued to Schatz et al. on Dec. 14, 1993, and U.S. Pat. No. 5,338,665 issued to Schatz et al. on Aug. 16, 1994, which are both incorporated herein by reference, refer to peptide libraries and screening methods which can be used to identify CCK A receptor ligands.

U.S. Pat. No. 5,395,750 issued to Dillon et al. on Mar. 7, 1995, which is incorporated herein by reference, refers to methods of producing proteins which bind to predetermined antigens. Such methods can be used to produce CCK A receptor ligands.

U.S. Pat. No. 5,223,409 issued to Ladner et al. on Jun. 29, 1993, which is incorporated herein by reference, refers to the directed evolution to novel binding proteins. Such proteins may be produced and screened as disclosed therein to identify CCK A receptor ligands.

U.S. Pat. No. 5,366,862 issued to Venton et al. on Nov. 22, 1994, which is incorporated herein by reference, refers to methods for generating and screening useful peptides. The methods herein described can be used to identify CCK A receptor ligands.

U.S. Pat. No. 5,340,474 issued to Kauvar on Aug. 23, 1994 as well as U.S. Pat. No. 5,133,866, U.S. Pat. No. 4,963,263 and U.S. Pat. No. 5,217,869, which are each incorporated herein by reference, can be used to identify CCK A receptor ligands.

U.S. Pat. No. 5,405,783 issued to Pirrung et al. on Apr. 11, 1995, which is incorporated herein by reference, refers to large scale photolithographic solid phase synthesis of an array of polymers. The teachings therein can be used. to identify CCK A receptor ligands.

U.S. Pat. No. 5,143,854 issued to Pirrung et al. on Sep. 1, 1992, which is incorporated herein by reference, refers to a large scale photolithographic solid phase synthesis of polypeptides and receptor binding screening thereof.

U.S. Pat. No. 5,384,261 issued to Winkler et al. on Jan. 24, 1995, which is incorporated herein by reference, refers to very large scale immobilized polymer synthesis using mechanically directed flow patterns. Such methods are useful to identify CCK A receptor ligands.

U.S. Pat. No. 5,221,736 issued to Coolidge et al. on Jun. 22, 1993, which is incorporated herein by reference, refers to sequential peptide and oligonucleotide synthesis using immunoaffinity techniques. Such techniques may be used to identify CCK A receptor ligands.

U.S. Pat. No. 5,412,087 issued to McGall et al. on May 2, 1995, which is incorporated herein by reference, refers to spatially addressable immobilization of oligonucleotides and other biological polymers on surfaces. Such methods may be used to identify CCK A Receptor ligands.

U.S. Pat. No. 5,324,483 issued to Cody et al. on Jun. 28, 1994, which is incorporated herein by reference, refers to apparatus for multiple simultaneous synthesis. The apparatus and method disclosed therein may be used to produce multiple compounds which can be screened to identify CCK A receptor ligands.

U.S. Pat. No. 5,252,743 issued to Barrett et al. on Oct. 12, 1993, which is incorporated herein by reference, refers to spatially addressable immobilization of anti-ligands on surfaces. The methods and compositions described therein may be used to identify CCK A receptor ligands.

U.S. Pat. No. 5,424,186 issued to Foder et al. on Jun. 13, 1995, which is incorporated herein by reference, refers to a very large scale immobilized polymer synthesis. The method of synthesizing oligonucleotides described therein may be used to identify CCK A receptor ligands.

U.S. Pat. No. 5,420,328 issued to Campbell on May 30, 1995, which is incorporated herein by reference, refers to methods of synthesis of phosphonate esters. The phosphonate esters so produced may be screened to identify compounds which are CCK A receptor ligands.

U.S. Pat. No. 5,288,514 issued to Ellman on Feb. 22, 1994, which is incorporated herein by reference, refers to solid phase and combinatorial synthesis of benzodiazepine compounds on a solid support. Such methods and compounds may be used to identify CCK A receptor ligands.

As noted above, CCK A receptor ligands may also be antibodies and fragments thereof. Indeed, antibodies raised to unique determinants of these receptors will recognize that protein, and only that protein and, consequently, can serve as a specific targeting molecule which can be used to direct novel diagnostics and therapeutics to this unique marker. In addition, these antibodies can be used to identify the presence of CCK A receptors or fragments of those receptors in biological samples, to diagnose the presence of colorectal cancer cells in vitro.

Once compounds have been identified as CCK A receptor ligands, there affinity to the CCK A receptor may be compared to that of CCK as well as their affinity to CCK B receptors. CCK A receptor specific ligands particularly useful according to the invention may thus be identified.

What is claimed is:

1. An in vitro method of determining whether a human individual has pancreatic cancer comprising the step of analyzing a sample of pancreatic tissue or fluid from a human to determine whether said sample contains mRNA that encodes CCK A receptor protein wherein the presence of mRNA that encodes CCK A receptor protein in the sample indicates that the human has pancreatic cancer.

2. The method of claim 1 wherein said mRNA that encodes said CCK A receptor protein is detected by an assay selected from the group consisting of: polymerase chain reaction and branched chain oligonucleotide hybridization.

3. An in vitro method of determining whether a human tumor cell is a human pancreatic tumor cell comprising detecting the presence of mRNA that encodes CCK A receptor protein in the human tumor cell, wherein the presence of mRNA that encodes CCK A receptor protein in the human tumor cell indicates that the human tumor cell may be a human pancreatic tumor cell.

4. The method of claim 3 wherein expression of said CCK A mRNA by said cells is determined by an assay selected from the group consisting of: polymerase chain reation wherein said human tumor cell is contacted with primers that selectively amplify mRNA or cDNA that encodes CCK A receptor protein and branched chain oligonucleotide hybridization.

5. The method of claim 1 wherein the sample is fluid from the pancreas.

6. The method of claim 5 wherein the presence of mRNA that encodes CCK A receptor protein is determined by polymerase chain reaction.

7. The method of claim 5 wherein the fluid from the pancreas is removed by an endoscopic retrograde cholangio pancreatography (ERCP) procedure.

8. The method of claim 7 wherein the presence of mRNA that encodes CCK A receptor protein is determined by polymerase chain reaction.

9. The method of claim 1 wherein said sample is pancreatic tissue.

10. The method of claim 9 wherein the presence of mRNA that encodes CCK A receptor protein is determined by polymerase chain reaction.

11. The method of claim 2 wherein the presence of mRNA that encodes CCK A receptor protein is determined by polymerase chain reaction.

12. An in vitro method of determining whether a human who has been diagnosed as having or who is suspected of having pancreatic cancer has metastatic pancreatic cancer comprising the step of analyzing a sample of blood, lymph tissue or lymph fluid from the human to determine whether the sample contains mRNA that encodes CCK A receptor protein, wherein the presence of mRNA that encodes CCK A receptor protein in the sample from a human who has been diagnosed as having or who is suspected of having pancreatic cancer indicates that the human has metastatic pancreatic cancer.

13. The method of claim 12 wherein the presence of mRNA that encodes CCK A receptor protein is determined by polymerase chain reaction.

14. The method of claim 12 wherein the sample is blood.

15. The method of claim 14 wherein the presence of mRNA that encodes CCK A receptor protein is determined by polymerase chain reaction.

16. The method of claim 12 wherein the sample is lymph tissue.

17. The method of claim 16 wherein the presence of mRNA that encodes CCK A receptor protein is determined by polymerase chain reaction.

18. The method of claim 12 wherein said sample is lymph fluid.

19. The method of claim 18 wherein the presence of mRNA that encodes CCK A receptor protein is determined by polymerase chain reaction.

20. The method of claim 12 wherein the individual has been diagnosed as having pancreatic cancer.

21. The method of claim 20 wherein the presence of mRNA that encodes CCK A receptor protein is determined by polymerase chain reaction.

22. The method of claim 20 wherein the sample is blood.

23. The method of claim 22 wherein the presence of mRNA that encodes CCK A receptor protein is determined by polymerase chain reaction.

24. The method of claim 20 wherein the sample is lymph tissue.

25. The method of claim 24 wherein the presence of mRNA that encodes CCK A receptor protein is determined by polymerase chain reaction.

26. The method of claim 20 wherein said sample is lymph fluid.

27. The method of claim 26 wherein the presence of mRNA that encodes CCK A receptor protein is determined by polymerase chain reaction.

* * * * *

UNITED STATES PATENT AND TRADEMARK OFFICE
CERTIFICATE OF CORRECTION

PATENT NO.   : 6,187,536 B1
DATED         : February 13, 2001
INVENTOR(S)  : David Weinberg et al.

It is certified that error appears in the above-identified patent and that said Letters Patent is hereby corrected as shown below:

Column 10,
Line 19, "131I" should be -- $^{131}I$ --
Line 22, "1910s" should be $^{191}Os$ --

Column 11,
Line 28, "recepto" should be -- receptor --

Column 13,
Line 6, "up to 20 gm…" starts a new paragraph

Column 14,
Line 24, "wherein " should be -- wherein --

Column 15,
Line 7, after "some embodiments of" the next sentence should follow.

Column 16,
Line 46, "therwise" should be -- otherwise --

UNITED STATES PATENT AND TRADEMARK OFFICE
CERTIFICATE OF CORRECTION

PATENT NO. : 6,187,536 B1
DATED : February 13, 2001
INVENTOR(S) : David Weinberg et al.

It is certified that error appears in the above-identified patent and that said Letters Patent is hereby corrected as shown below:

<u>Column 17,</u>
Line 16, after "present" delete the colon -- : --

<u>Column 21,</u>
Line 26, after "solid" the next word -- phrase -- should follow.

<u>Column 23,</u>
Line 17, "1251" should be -- $^{125}$I --

<u>Column 26,</u>
Line 59, ".251" should be -- $^{125}$I --

Signed and Sealed this

Fourth Day of September, 2001

Attest:

*Nicholas P. Godici*

NICHOLAS P. GODICI
*Acting Director of the United States Patent and Trademark Office*

*Attesting Officer*